US011471112B2

(12) United States Patent
Gruentzig

(10) Patent No.: US 11,471,112 B2
(45) Date of Patent: Oct. 18, 2022

(54) MOBILE APPLICATION FOR WEARABLE DEVICE

(71) Applicant: Legionarius, LLC, Sudbury, MA (US)

(72) Inventor: Alexander Gruentzig, Sudbury, MA (US)

(73) Assignee: Legionarius, LLC, Wilmington, DE (US)

( * ) Notice: Subject to any disclaimer, the term of this patent is extended or adjusted under 35 U.S.C. 154(b) by 145 days.

(21) Appl. No.: 16/682,044

(22) Filed: Nov. 13, 2019

(65) Prior Publication Data

US 2020/0237318 A1 Jul. 30, 2020

Related U.S. Application Data

(60) Provisional application No. 62/770,629, filed on Nov. 21, 2018.

(51) Int. Cl.
*A61B 5/00* (2006.01)
*G16H 40/67* (2018.01)
(Continued)

(52) U.S. Cl.
CPC .......... *A61B 5/7282* (2013.01); *A61B 5/0022* (2013.01); *A61B 5/02055* (2013.01);
(Continued)

(58) Field of Classification Search
CPC . A61B 17/12; A61B 17/1325; A61B 17/1355; A61B 2017/00557;
(Continued)

(56) References Cited

U.S. PATENT DOCUMENTS 451,197 A 4/1891 Robare
1,042,314 A 10/1912 Brion
(Continued)

FOREIGN PATENT DOCUMENTS

WO WO-92/13074 A1 8/1992
WO WO-2006/086402 A2 8/2006
(Continued)

OTHER PUBLICATIONS

International Search Report and Written Opinion for International Patent Application No. PCT/US2015/028912, dated Dec. 29, 2015 (21 pages).
(Continued)

*Primary Examiner* — Jonathan T Kuo

(57) ABSTRACT

Featured are devices (e.g., peripheral devices) and systems that interact with a device having sensors (e.g., a wearable device or device configured for use with a piece of equipment, such as a vehicle) to receive and process data (e.g., physiological data) from the sensors. Also featured are computer implemented methods including software (e.g., an application) for receiving and processing data by the peripheral device. An application that communicates with the device (e.g., wearable device or equipment device) and sensor information processed by the application or a device running or accessing the application provides situational awareness for users in adverse conditions, such as during combat or wartime. The wearable device may include one or more inflatable bladders configured to apply pressure to a wound site for treatment.

25 Claims, 33 Drawing Sheets

(51) Int. Cl.
| | |
|---|---|
| *A61B 5/0205* | (2006.01) |
| *A61B 17/12* | (2006.01) |
| *G06F 3/048* | (2013.01) |
| *H04L 9/40* | (2022.01) |
| *H04W 12/33* | (2021.01) |
| *A61B 5/021* | (2006.01) |
| *A61B 5/024* | (2006.01) |
| *A61B 5/08* | (2006.01) |
| *A61B 5/026* | (2006.01) |
| *A61B 5/145* | (2006.01) |
| *A61B 17/00* | (2006.01) |
| *H04W 12/63* | (2021.01) |

(52) U.S. Cl.
CPC .......... *A61B 5/4836* (2013.01); *A61B 5/7425* (2013.01); *A61B 17/12* (2013.01); *G06F 3/048* (2013.01); *G16H 40/67* (2018.01); *H04L 63/083* (2013.01); *H04W 12/33* (2021.01); *A61B 5/021* (2013.01); *A61B 5/026* (2013.01); *A61B 5/02438* (2013.01); *A61B 5/0816* (2013.01); *A61B 5/14542* (2013.01); *A61B 5/6804* (2013.01); *A61B 2017/00557* (2013.01); *A61B 2017/12004* (2013.01); *H04W 12/63* (2021.01)

(58) Field of Classification Search
CPC ........ A61B 2017/12004; A61B 5/0022; A61B 5/02055; A61B 5/021; A61B 5/02438; A61B 5/026; A61B 5/0816; A61B 5/14542; A61B 5/4836; A61B 5/6804; A61B 5/7282; A61B 5/7425; A61B 5/746; A61B 5/747; G06F 3/048; G16H 40/63; G16H 40/67; G16H 50/30; H04L 63/083; H04W 12/009; H04W 12/069; H04W 12/30; H04W 12/63
See application file for complete search history.

(56) References Cited

U.S. PATENT DOCUMENTS

| | | |
|---|---|---|
| 3,193,842 A | 7/1965 | Bell |
| 3,933,150 A | 1/1976 | Kaplan et al. |
| 5,090,053 A | 2/1992 | Hayes |
| 5,195,752 A | 3/1993 | Reeves et al. |
| 5,636,378 A | 6/1997 | Griffith |
| 5,867,842 A | 2/1999 | Pinsley et al. |
| 6,012,162 A | 1/2000 | Bullat |
| 6,032,299 A | 3/2000 | Welsh |
| 6,042,147 A | 3/2000 | Nishijima et al. |
| 6,198,394 B1 * | 3/2001 | Jacobsen ............... A61B 5/1112 340/573.1 |
| 6,349,201 B1 | 2/2002 | Ford |
| 6,757,916 B2 | 7/2004 | Mah et al. |
| 6,939,314 B2 | 9/2005 | Hall et al. |
| 6,997,218 B1 | 2/2006 | Garcia et al. |
| 7,056,179 B2 | 6/2006 | Courtney |
| 7,288,011 B2 | 10/2007 | Ganley |
| 7,329,792 B2 | 2/2008 | Buckman et al. |
| 7,548,168 B2 | 6/2009 | Ishikawa et al. |
| D596,829 S | 7/2009 | Miller |
| 7,921,472 B2 | 4/2011 | Mazzarolo |
| 8,079,247 B2 | 12/2011 | Russell et al. |
| 8,231,421 B1 | 7/2012 | Hubbard et al. |
| 8,591,275 B2 | 11/2013 | Gonsalves et al. |
| D743,146 S | 11/2015 | Yerby |
| 9,242,093 B1 | 1/2016 | Sherman |
| D775,786 S | 1/2017 | Trabert |
| 9,600,995 B2 * | 3/2017 | Gaidar ............... G08B 21/0453 |
| 10,052,223 B2 | 8/2018 | Turner |
| D905,935 S | 12/2020 | Gruentzig |
| 10,856,884 B2 * | 12/2020 | Carabajal ............. A61B 5/0036 |
| 10,874,152 B2 * | 12/2020 | Gruentzig ................ A41D 1/04 |
| 11,051,565 B2 | 7/2021 | Gruentzig |
| 2005/0067816 A1 | 3/2005 | Buckman |
| 2007/0061941 A1 | 3/2007 | Makabe et al. |
| 2008/0105114 A1 | 5/2008 | Gabrys |
| 2010/0083733 A1 | 4/2010 | Russell et al. |
| 2010/0274100 A1 * | 10/2010 | Behar .................. A61B 5/6804 600/301 |
| 2011/0204114 A1 | 8/2011 | Miller |
| 2012/0060260 A1 | 3/2012 | Kochling |
| 2012/0102630 A1 | 5/2012 | Anderson |
| 2012/0118449 A1 | 5/2012 | Barnes et al. |
| 2012/0144934 A1 | 6/2012 | Russell et al. |
| 2012/0180179 A1 | 7/2012 | Lee et al. |
| 2012/0246788 A1 | 10/2012 | Harrell et al. |
| 2013/0058906 A1 | 3/2013 | Turzi |
| 2013/0131566 A1 | 5/2013 | Bodansky |
| 2013/0210297 A1 | 8/2013 | Maas et al. |
| 2014/0023579 A1 | 1/2014 | van Vliet et al. |
| 2014/0236221 A1 | 8/2014 | Zhadkevich |
| 2015/0173433 A1 | 6/2015 | Mazzarolo et al. |
| 2015/0374060 A1 | 12/2015 | Morgan |
| 2016/0008206 A1 | 1/2016 | Devanaboyina |
| 2016/0379461 A1 * | 12/2016 | Gaidar ................. A43B 3/0005 340/573.1 |
| 2017/0049164 A1 * | 2/2017 | Gruentzig .............. A41D 13/02 |
| 2017/0193858 A1 | 7/2017 | Segall |
| 2018/0214161 A1 * | 8/2018 | Carabajal ........... A61B 17/1355 |
| 2019/0069623 A1 | 3/2019 | Kuntz |
| 2019/0208841 A1 | 7/2019 | Gruentzig |
| 2020/0247513 A1 | 8/2020 | Garner et al. |
| 2020/0277033 A1 | 9/2020 | White |
| 2021/0145450 A1 * | 5/2021 | Gru ...................... A61B 5/6806 |

FOREIGN PATENT DOCUMENTS

| | | |
|---|---|---|
| WO | WO-2007/142887 A1 | 12/2007 |
| WO | WO-2015/183470 A2 | 12/2015 |
| WO | WO-2018/213615 A2 | 11/2018 |

OTHER PUBLICATIONS

International Preliminary Report on Patentability for International Patent Application No. PCT/US2015/028912, dated Nov. 1, 2016 (11 pages).

International Search Report and Written Opinion for International Patent Application No. PCT/US2018/033241, dated Aug. 13, 2018 (11 pages).

* cited by examiner

FIG. 32

MOBILE APPLICATION FOR WEARABLE DEVICE

BACKGROUND OF THE INVENTION

Hemorrhage from vascular injuries in the proximal extremities, pelvis, and abdomen is extremely difficult to triage in the field outside of medical facilities. While the treatment of such injuries is challenging when they occur in civilian populations, they are even more difficult to treat in combat situations. While improvements in body armor have reduced mortality from combat injuries to the chest, the incidence of penetrating injuries to the extremities and their associated mortality remain high. Wearable devices have been developed to protect a person from and/or treat injuries sustained in combat situations. However, when the person is injured, the appropriate parties are not always promptly notified of the injury. The time between injury and proper care is a critical window that can significantly affect the outcome. If the window is too long, the person may die.

Furthermore, other hardware, devices, or equipment, such as vehicles (e.g., military vehicles, drones, and aircraft), could benefit from increased situational awareness that would allow for an increase in response time following a catastrophic episode (e.g., destruction caused by a bomb or ballistic impact). Accordingly, new devices, systems, and methods are needed to interact with wearable devices or other equipment (e.g., vehicles) in order to relay critical information to a person wearing the device or operating the equipment, as well as to third party responders, such as medical professionals.

SUMMARY OF THE INVENTION

Featured is a computer implemented method for presenting data (e.g., physiological data regarding the health state of a subject or operational status of a device or equipment) by using an application operating on a peripheral device including a graphical user interface. The method may include acquiring the data (e.g., physiological data) from one or more sensors located within or on a device (e.g., wearable device or a device configured for use in or on a device or equipment, such as a vehicle) and displaying the physiological data on the graphical user interface. If configured for use with a wearable device, the wearable device may include one or more inflatable bladders that is adorned by the subject.

The data (e.g., physiological data) may be selected from one or more of ballistic impact site (e.g., on the subject or the device or equipment (e.g., a vehicle), impact force, source or direction of impact, injury type, geolocation, body or device/equipment position, respiratory rate, heart rate, and blood pressure. The physiological data may be displayed to the subject or another person, such as a team member or a third party responder. The one or more sensors may include an impact detection sensor, a blood flow sensor, a temperature sensor, a heart rate sensor, a blood pressure sensor, an oxygen saturation sensor, or a vital sign monitoring (VSM) sensor.

The method may further include activating inflation of the one or more inflatable bladders in the wearable device in response to the physiological data. For example, a signal producing the activation may be received from another user communicating to the peripheral device of the subject.

The application may include a mode that displays a map including a geographical location of the subject or equipment/device. The map may further include a geographical location of one or more other users or devices, e.g., vehicles. The application may include a mode that displays information of the subject (e.g., name, age, date, time, unit, blood type, and allergy). The application may include a mode that displays a system status (e.g., power, connectivity signal, impact detection sensor status, and VSM sensor status of the wearable device or the peripheral device). The application may include a mode that displays one or more system settings (e.g., on/off switch and/or a sensitivity toggle for the wearable device). The on/off switch may control an impact sensor, a VSM sensor, and/or an alert function of the wearable device.

The application may include a mode that displays a cause of injury to the subject (e.g., artillery, a burn, a fall, a grenade, a gunshot wound, an improvised explosive device, a landmine, a motor vehicle collision, or a rocket propelled grenade) or a cause of damage to the equipment/device (e.g., artillery, a burn, a grenade, a gunshot, an improvised explosive device, a landmine, a motor vehicle collision, or a rocket propelled grenade). The application may include a mode that displays a location of injury on the subject (e.g., head, arm, leg, torso, and back) or a location of damage to the equipment/device. The application may include a mode that displays signs and/or symptoms of the subject (e.g., blood pressure, pulse and oxygen saturation, alert, voice, pain, unresponsive (AVPU), and pain scale). The application may include a mode that displays one or more treatments performed on the subject (e.g., extremity tourniquet, junctional tourniquet, pressure dressing, hemostatic dressing, intact, cricothyrotomy (CRIC), supraglottic airway (SGA), nasopharyngeal airway (NPA), endotracheal tube, oxygen, chest tube, chest seal, needle injection, fluid administration, blood transfusion, combat pill pack, eye shield, splint, and hypothermia prevention). The application may include a mode that displays one or more medicines administered to the subject (e.g., an analgesic or antibiotic). The application may include a mode that displays repairs needed for or made to the equipment/device.

The application may include a mode that continuously displays physiological data of the subject (e.g., heart rate and/or respiration rate) or data relevant to the operational status of the equipment/device.

In any of the above embodiments, the graphical user interface may be a touch-screen graphical user interface. The display on the touch-screen graphical user interface may be editable.

The application may include a mode to transmit the physiological data of the subject to a third party responder. The application may include a mode to request medical evacuation of the subject. The mode to request medical evacuation may transmit information of the subject including one or more of geolocation, radio frequency, nationality, treatment status, military status, special equipment request, wartime security status, method of site marking, and site contamination status.

In some embodiments,
 a) the treatment status includes urgent, urgent surgery required, priority, routine, or convenience;
 b) the nationality includes US or non-US;
 c) the military status includes military, civilian, or enemy prisoner of war;
 d) the special equipment request includes a hoist, extraction equipment, or a ventilator;
 e) the wartime security status includes no enemy troops, possible enemy, enemy in area and proceed with caution, or enemy in area and armed escort required;

f) the method of site marking includes a panel, pyrotechnic signal, or a smoke signal; and/or g) the site contamination status includes chemical, biological, radiological, or nuclear contamination.

The application may include a security feature (e.g., a login with a username, password, or other security code). The application may be performed on a cloud-based device or a server.

The peripheral device running or accessing the application may include one or more processors coupled to the display. The peripheral device running or accessing the application may include a non-transient memory storing instructions that, when executed by the one or more processors, causes the one or more processors to perform one or more operations, such as processing sensor data to produce the physiological data and displaying the physiological data on the graphical user interface.

Also featured is a peripheral device including a display, one or more processors coupled to the display, and a non-transient memory storing instructions. The instructions, when executed by the one or more processors, may cause the one or more processors to perform operations. These operations may include rendering a graphical user interface in the display, processing sensor data to produce physiological data, receiving an input of physiological data to the graphical user interface, and/or displaying the physiological data on the graphical user interface. The peripheral device may be configured for wired or wireless communication with one or more sensors located within or on a wearable device including one or more inflatable bladders.

The peripheral device may be configured to provide physiological data selected from one or more of ballistic impact site, impact force, source or direction of impact, injury type, geolocation, body position, respiratory rate, heart rate, and blood pressure. The peripheral device may be configured to display the physiological data to a subject wearing the wearable device or a third party responder. The peripheral device may be configured to cause the one or more inflatable bladders in the wearable device to inflate in response to the physiological data. The peripheral device may also be configured to provide operational data on equipment/device selected from one or more of ballistic impact site, impact force, source or direction of impact, damage type, geolocation or position, and operational status/functional state. The peripheral device may be configured to perform the computer implemented method of any of the above embodiments.

Also featured is a system including the peripheral device of any of the above embodiments and a wearable device including one or more bladders or the peripheral device of any of the above embodiments and a piece of equipment or other device (e.g., a vehicle, drone, or aircraft).

Also featured is a system including a plurality of the peripheral devices of any of the above embodiments, each of which is independently running the application. The plurality of peripheral devices may be configured to communicate with each other (e.g., as a team, such as a military unit). The plurality of peripheral devices may be configured to communicate wirelessly with each other. The system may further include a plurality of wearable devices, each of which is independently configured to communicate with any one, or all, of the plurality of peripheral devices. The system may be configured such that a designated one of the plurality of peripheral devices is configured to communicate with a designated one of a plurality of the wearable devices.

The system may further include a plurality of the wearable devices, each of which may be independently configured to communicate with any one, or all, of the plurality of peripheral devices. Each of the plurality of peripheral devices may be configured to control any one, or all, of said plurality of the wearable devices. For example, a designated one of the plurality of peripheral devices may be configured to control a designated one of said plurality of the wearable devices. The control may include activation of inflation of the one or more bladders of the plurality of the wearable devices. The plurality of peripheral devices may be configured to communicate with any one, or all, of a plurality of the wearable devices.

In any of the above systems, the communication may include transmission of physiological data or other indicia regarding one or more users of the system.

BRIEF DESCRIPTION OF THE DRAWINGS

Figure 32:
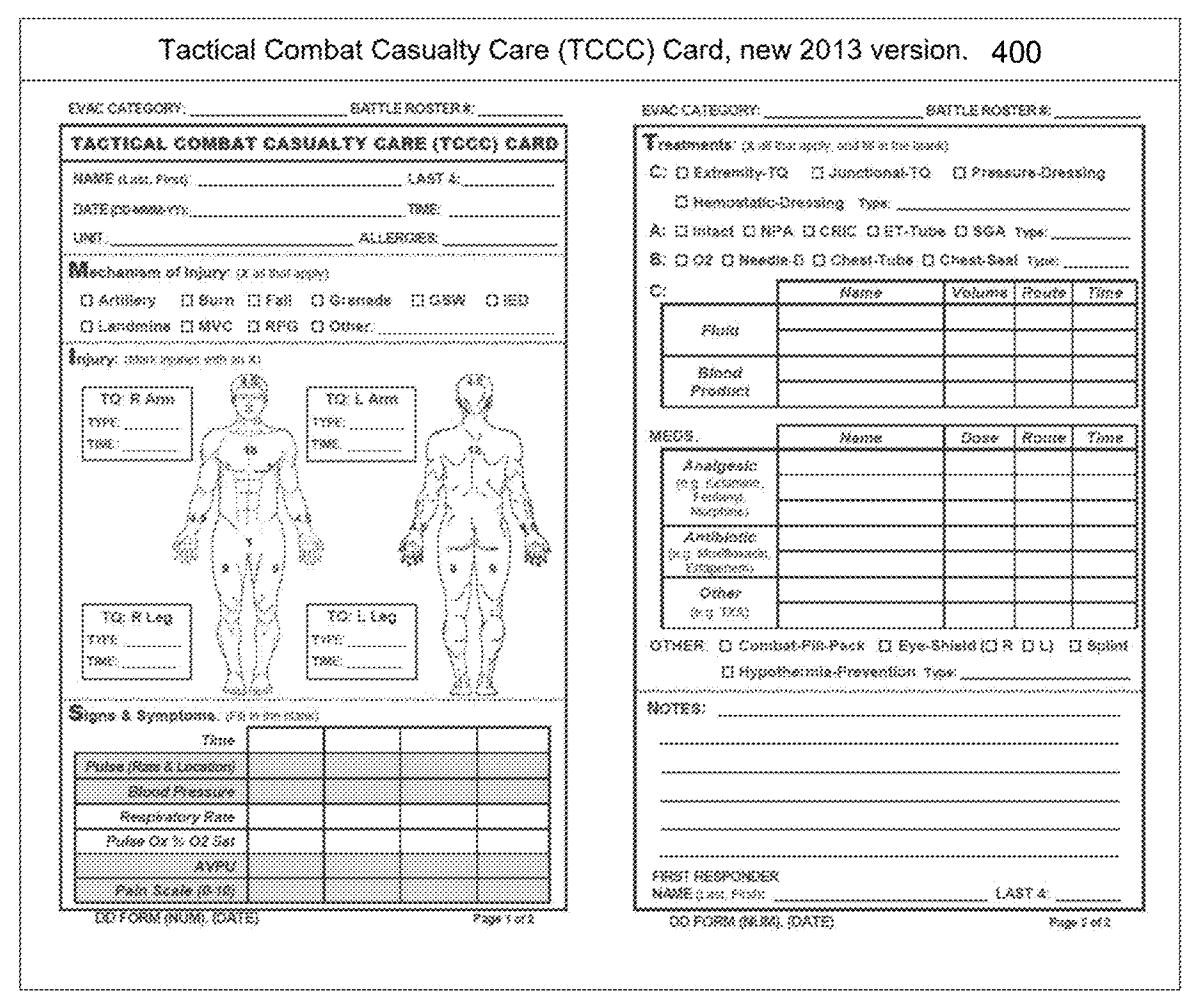

FIG. 32 is TCCC card 400. The information input onto the graphical user interface, e.g., that is displayed on a peripheral device, can be output onto TCCC card 400 to summarize all of the information regarding a user of the system for a third party responder.

DETAILED DESCRIPTION

Figure 1:
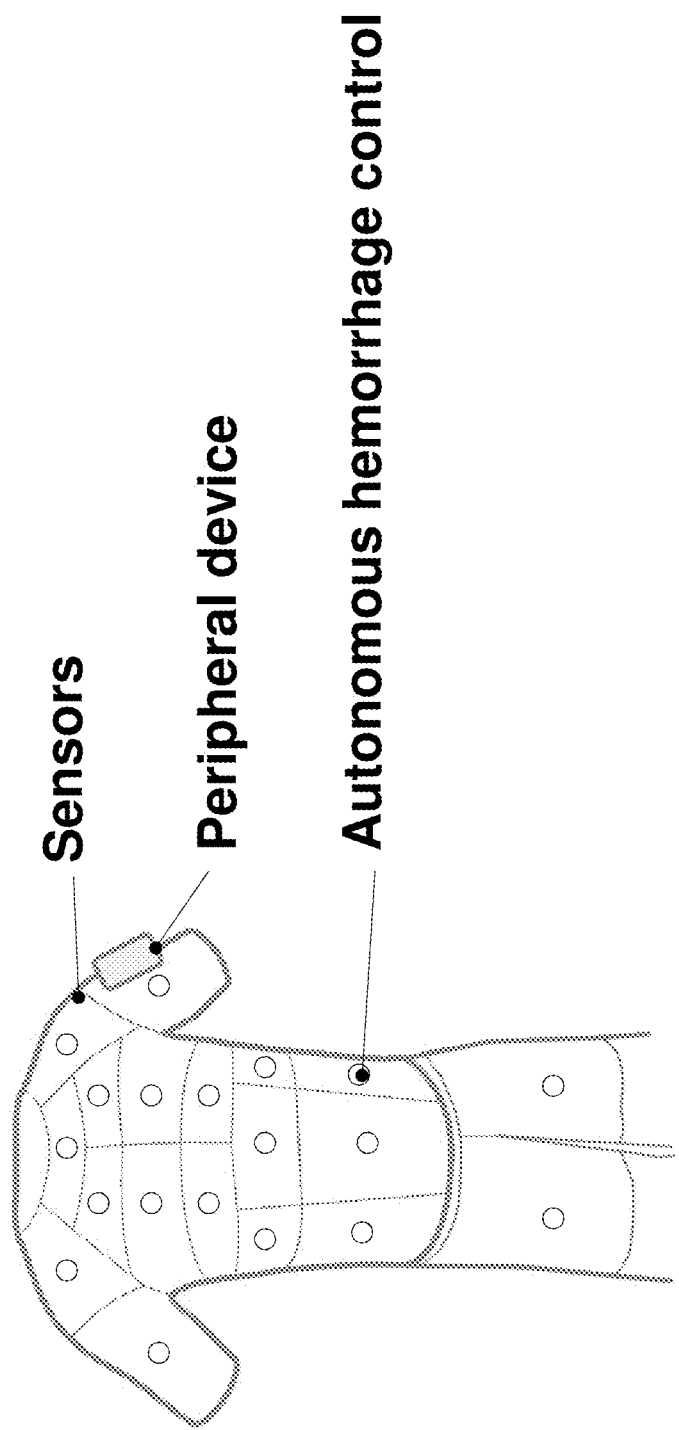
FIG. 1 is a schematic drawing of a wearable device that is configured to interact with a mobile application device. The wearable device includes sensors or regions of sensors that instantly detect a triggering event, such as an impact. A signaling device on the wearable device then transmits diagnostic information to a third party responder. The wearable device also includes autonomous hemorrhage control that is activated by the signal from the sensors.
Figure 2:
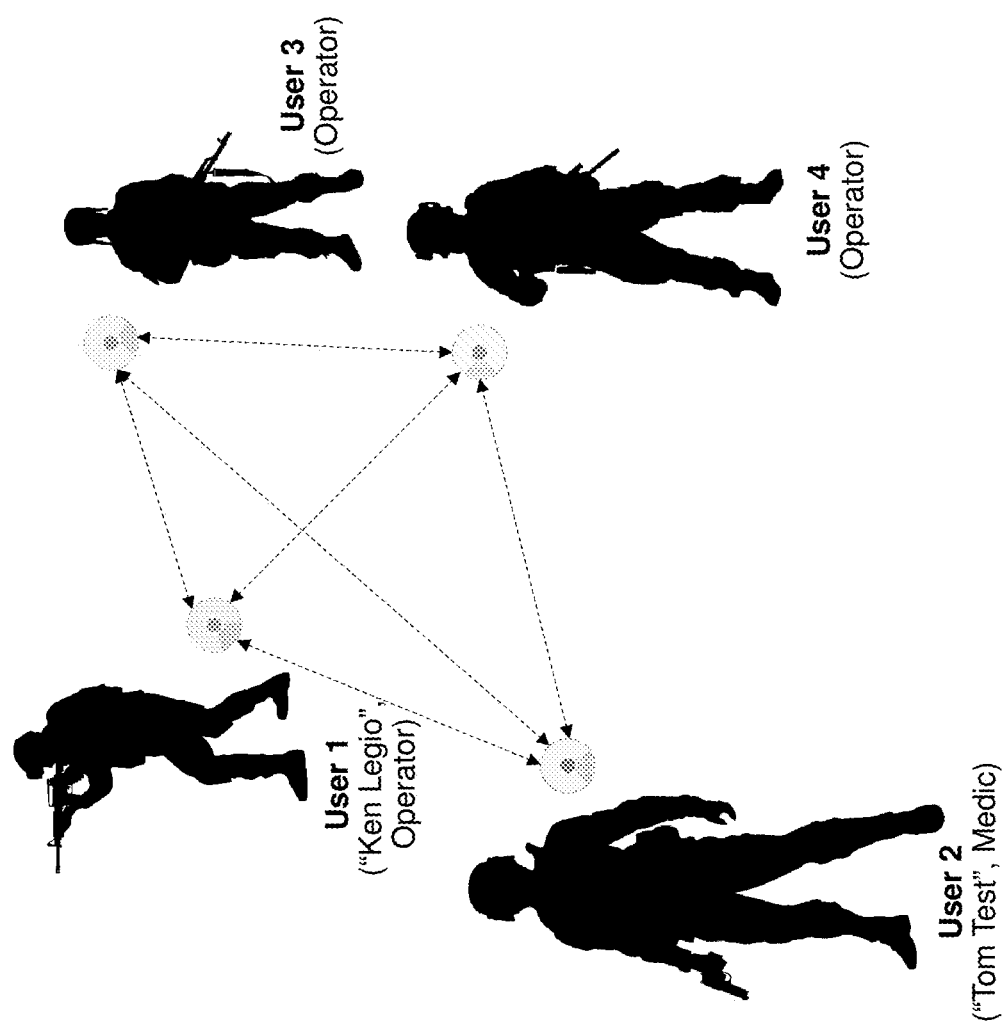
FIG. 2 is a schematic drawing showing a network of a team of four operators with a wearable device configured to interact with a peripheral device application. Each wearable device is configured to transmit a GPS location for the operator, which is transmitted to each member of the team.

Featured are devices and systems configured to transmit to and receive input from sensors on a device (e.g., a wearable device, such as a garment, or a device configured for use with equipment, such as a vehicle (e.g., an automobile, tank, or aircraft) or a drone), and computer implemented methods using the devices and systems. The devices and systems can receive and process data (e.g., physiological data) from sensors on, e.g., on the device (e.g., the wearable device or equipment device, e.g., on a vehicle) (FIG. 1). The devices and systems may utilize software (e.g., an application) running on the devices and systems or accessible from the device or system using, e.g., a cloud-based interface, that communicates with the device. Sensor information processed by the application or a device running the application can be used to provide situational awareness for users under a variety of conditions, such as adverse conditions, in particular during combat or wartime. This information can be presented to the user of the device, other team members operating in concert (e.g., on a mission) with the user, or a third party (FIG. 2).

In the event that an episode (e.g., an injury, such as a catastrophic injury, for example, a ballistic impact) occurs to the user wearing or operating the device, the sensors present on the device (e.g., wearable device or equipment device, e.g., vehicle device) can instantly detect various indicia related to the details of the episode (e.g., severity of impact, location of impact, direction or source of impact, details of injury) and/or the health status of the device or user (e.g., physiological indicia, biometric data, operational status (e.g., broken or damaged components)). The sensor information can be instantly collected and subsequently processed by an algorithm e.g., using an application, such as a software application. The application may be present on a peripheral device (e.g., that is worn or operated by the user) or may be present on a separate device that communicates with the sensors. For example, the sensors may be connected to a transmitter and/or receiver that transmits the raw data from the sensors that is then processed by the application. The application can then render this information on a graphical user interface (e.g., a touch screen graphical user interface). This information can be presented to the user and/or distributed to other relevant parties to provide other team members with an accurate depiction of the health status of the user. This information allows the third party to effectively monitor the status (e.g., health status) of the user or the operational status of the device (e.g., equipment, such as a vehicle) and provide the appropriate response or care, if needed, to treat the user or attend to or repair the equipment (e.g., a vehicle).

The device with one or more sensors may be configured as a wearable device with one or more (e.g., 2, 3, 4, 5, 6, 7, 8, 9, 10, or more) bladders. The bladders may be used for autonomous hemorrhage control to prevent fluid (e.g., blood) loss. For example, if the user wearing the wearable device suffers an episode (e.g., an injury, such as a catastrophic injury, for example, a ballistic impact), the sensors on the wearable device can instantly detect information about the episode. For example, the sensors can detect the velocity of the ballistic impact and the location and nature of the injury (e.g., torso, e.g., entrance or exit wound). A transmitter and/or receiver on the wearable device processes information about the impact and transmits a signal to trigger inflation of the bladders at or near the site of the injury. Inflation of the bladders applies pressure on the wound thereby preventing or reducing fluid (e.g., blood) loss (e.g., hemorrhage). This feature provides an automated injury response in the event that the injured user cannot care for himself and/or a third party responder or team member is too far away to immediately apply pressure to the wound.

The device may be configured as a device present on an inanimate object, such as a vehicle (e.g., car, truck, plane, helicopter, boat, motorcycle, and drone), or a piece of equipment (e.g., backpack, barrel, and canister). The device may include sensors, such as impact detection sensors, that provide situational awareness regarding the health or functional status of the device or equipment. For example, if configured for a vehicle and the vehicle experiences an impact detection (e.g., from a ballistic impact), the sensors on device may collect data regarding the impact (e.g., direction of impact, force of impact, location of impact). This data may then be used to alert the operator of the vehicle or a team member (e.g., third party responder) that the vehicle has an issue (e.g., broken or damaged component, flat tire, or armor defect).

The devices, systems, and methods described herein can be used to present data (e.g., physiological data) regarding the health state of a subject or operational status of equipment or a device (e.g., a vehicle), which can be accessed, controlled, or monitored with the assistance of an application (e.g., software) running on a peripheral device or accessible by a peripheral device (e.g., using wireless or cloud-based access). The subject may be wearing a wearable device that includes one or more sensors located on or within the garment. The application may operate on a device (e.g., peripheral device) with a graphical user interface including a display. The graphical user interface may be a touch-screen graphical user interface. The device may include one or more processors coupled to the display and a memory storing instructions that, when executed by the one or more processors, causes the one or more processors to perform specific operations. The processors may be configured to acquire the physiological data from one or more sensors located within or on the wearable device and to display the physiological data on the graphical user interface.

The components of the devices and systems described herein, such as a peripheral device configured to run or access the application, a graphical user interface, an information processing unit, a wearable device, equipment or a device (e.g., configured for use with a vehicle), and sensors, are described in more detail below. These devices and systems may also be used with the computer implemented methods also described in more detail below.

Peripheral Device

A device (e.g., a wearable device or a device configured for use with a piece of equipment, such as a vehicle) can be configured as a system for use with a peripheral device running or accessing software (e.g., an application). The peripheral device may be any suitable medium for computing and/or displaying information. The peripheral device may be a smartphone (e.g., ANDROID™, iPhone®), tablet (iPad®), computer, cloud-based device (e.g., server), a web-based device, smart glasses, or other information processing device. The peripheral device may be programmed with a software application (e.g., that can be downloaded into the resident memory of the device and run locally on the peripheral device) to receive data that is detected by the sensors on the wearable device and then transmitted (e.g., with a transmitter) to the peripheral device. The peripheral device may include a display, one or more processors coupled to the display, and a memory storing instructions that, when executed by the one or more processors, causes the one or more processors to perform a programmed operation. This operation may be used to direct an output action (e.g., bladder inflation, signaling for assistance). The operation may include rendering a graphical user interface in the display, receiving an input of data (e.g., physiological data or operational status data) to the graphical user interface, and displaying the data on the graphical user interface. The peripheral device may be configured for wired or wireless communication with one or more sensors located within or on the device (e.g., the wearable device). Alternatively, or in addition, the device and/or the peripheral device may include a transmitter and/or receiver to transmit the data detected by the sensors to the peripheral device. The transmitter may be, e.g., a smart chip, and it can be configured for wired or wireless communication, e.g., through a Bluetooth or Wi-Fi connection, to the peripheral device. The user of the device (e.g., the wearable device or the equipment) may use the peripheral device or a third party may use the peripheral device.

Figure 3:
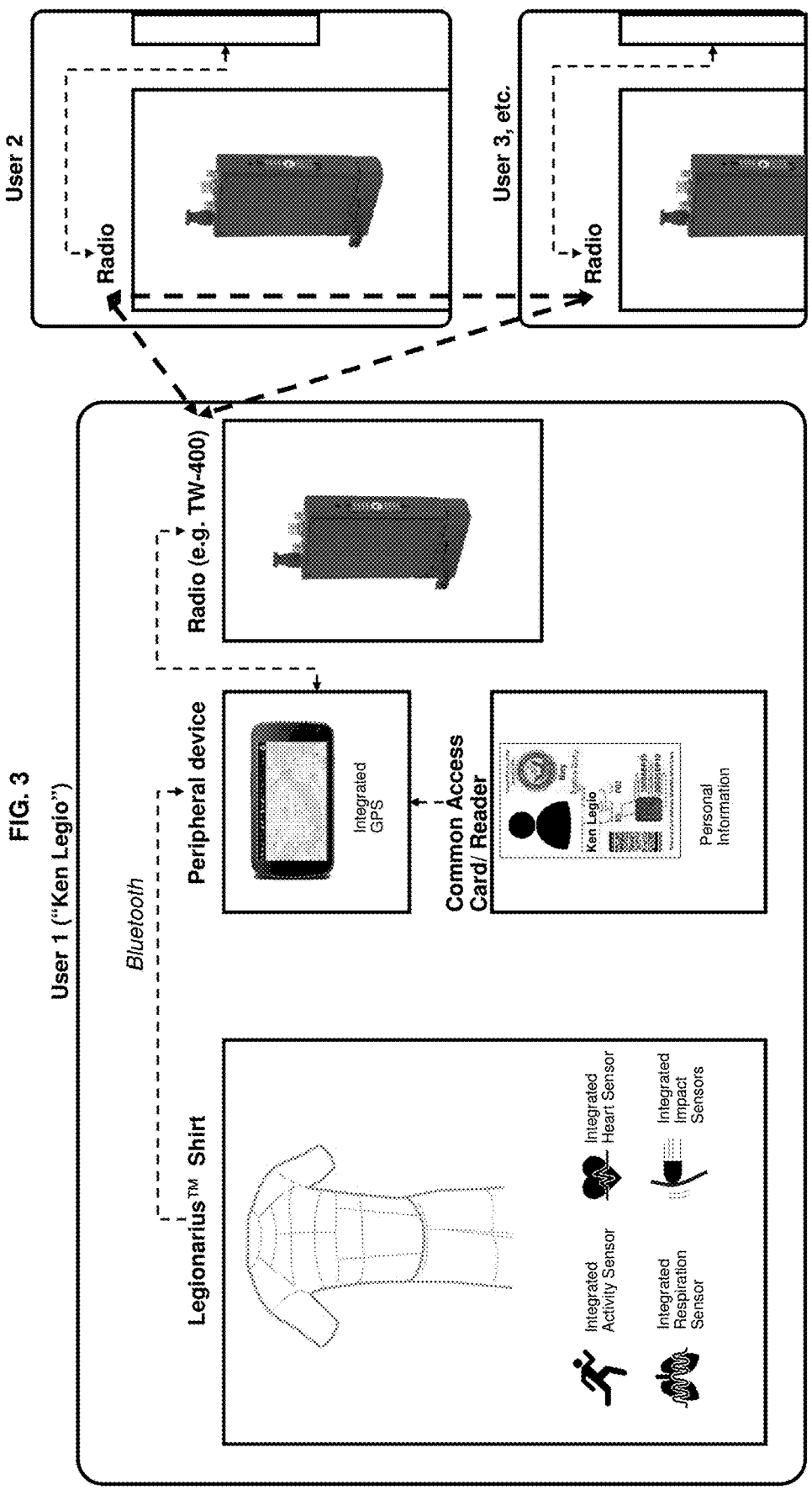
FIG. 3 is a schematic drawing showing a system that includes a wearable device (e.g., a shirt), a peripheral device running or accessing an application, a common access card reader with personal information, and optionally, a radio for external communication for a first user ("User 1"). The wearable device includes an integrated activity sensor, heart sensor, respiration sensor, and impact sensors. Other users optionally have a radio that can communicate with the first user. The other users may also have a peripheral device that receives health indicia that is transmitted from the first user's peripheral device

The peripheral device may access the application on a remote server, e.g., with a cloud-based connection. The device (e.g., the wearable device) may include a peripheral device, e.g., attached thereto or separate from the device (e.g., as a handheld device). For example, FIG. 3 shows a system including a wearable device that includes integrated activity sensors, respiration sensors, heart sensors, and impact detection sensors. The wearable device may be connected to the peripheral device (e.g., smartphone) running or accessing a software program via a Bluetooth connection. The peripheral device may include a mechanism to read an identification card (e.g., by scanning a barcode or QR code) so that important personal information about a user (e.g., medical history, allergies, handicap) is instantly uploaded to the peripheral device running or accessing the application.

Additionally, the peripheral device running the application can be configured to communicate (e.g., through a wired or wireless connection, e.g., through a Bluetooth, Wi-Fi, and/or internet connection) with a database that contains data collected by the device (e.g., the wearable device) or with another system that receives and processes the data and conveys the information to the peripheral device and/or displays the information on the graphical user interface. Data collected by the device (e.g., the wearable device), such as data collected by the sensor(s), may be stored non-transiently in the database, the peripheral device, or other storage medium.

Application

The peripheral device may be configured to run or access software (e.g., an application). The application may include any suitable computing instructions (e.g., code) that causes the peripheral device to perform an operation. The user of the peripheral device, a third party responder, medical aide, or other relevant personnel may be running the application on his/her peripheral device (e.g., smartphone) to track information about the subject wearing or operating the device (e.g., wearable device or equipment, such as a device configured for use with a vehicle). For example, the application may be programmed on and/or running locally on the peripheral device. Alternatively, or additionally, the application may not be programmed on and/or running locally on the peripheral device. The application may include a security feature or login that requires the user to input, e.g., a username or password to access the peripheral device and/or the application. The application may, alternatively, be running on a cloud-based or internet-based device and may optionally require log-in credentials to access the remote connection.

Figure 33:
FIG. 33 is a photograph of an ANDROID™ smartphone running an ANDROID™ tactical assault kit (ATAK) application.

The wearable device or equipment, such as a device configured for use with a vehicle, may be configured to communicate with a peripheral device, such as a smartphone (e.g., ANDROID™ or iPhone®) running or accessing an application. The smartphone may be running an ANDROID™ tactical assault kit (ATAK) application or a similar application (FIG. 33). ATAK is an ANDROID™ smartphone geo-spatial infrastructure application built using NASA World Wind. The application (e.g., ATAK application) provides situational awareness within both civilian and military arenas. The application may have a plugin architecture which allows developers to add functionality to the application. When used with the wearable devices described herein, the application (e.g., ATAK application) can display indicia related to the user or an episode (e.g., catastrophic episode, such as a ballistic impact) experienced by the user, such as projectile velocity, impact location, acceleration (e.g., moving or still) and orientation (e.g., prone or supine) information of the user, respiration rate, heart rate, user information, and geolocation. The device transmits essential physiological indicia and sensor data to the user or to a third party responder using a smartphone running the application (e.g., ATAK application).

The application running on or accessible by the peripheral device may contain features used to control the functionality of the device (e.g., the wearable device or equipment, such as a device configured for use with a vehicle) or the sensors of the device (e.g., the wearable device or equipment, such as a device configured for use with a vehicle). Some features include a system on/off or reset switch, a power level indicator, the ability the turn certain sensors or regions of sensors or bladders on or off, or adjust the sensitivity of the sensors. The user of the application can track data from the sensors in real time or observe data over a long time period, and the information may be stored for later analysis. The application may be used to track the health status of an individual or the operational status of equipment, such as a vehicle, for example, by measuring various parameters, e.g., physiological parameters, such as heart rate or acceleration, or the condition of the individual, or operational parameters, such as the function or status of component parts of the equipment. The application can be made available for download (e.g., from the internet or the cloud, e.g., a remote server) on a peripheral device.

Figure 9:
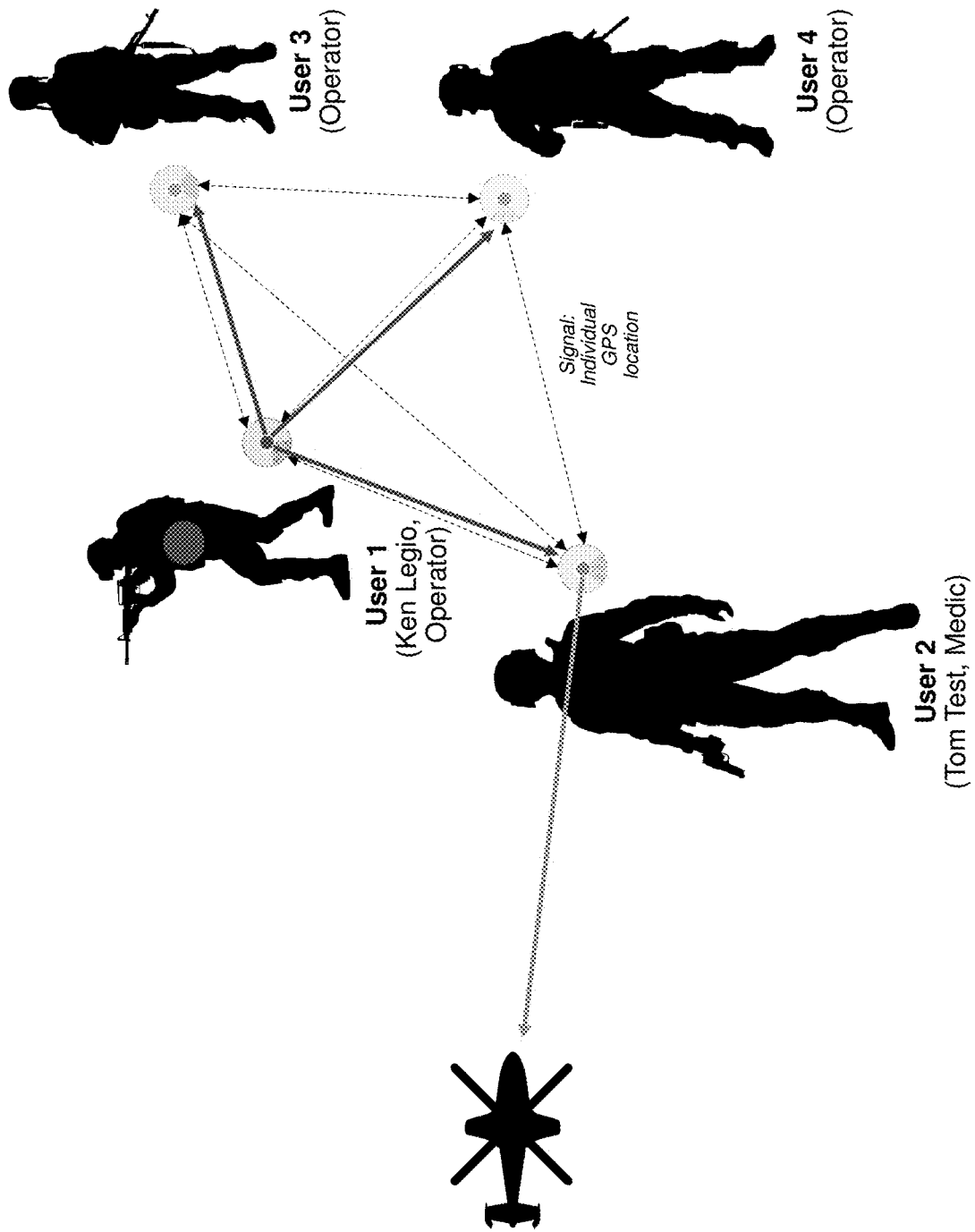
FIG. 9 is schematic drawing showing a network of a team of four operators with a wearable device configured to interact with a peripheral device application. Each wearable device is configured to transmit a GPS location for the operator, which is transmitted to each member of the team. Once a high velocity impact is detected by a sensor of a device worn by User 1, the device transmits a signal to the peripheral device of User 1. The application, which is active on the peripheral device, then transmits a signal to each member of the team, who also have the application active on their peripheral devices. The transmitted information includes indicia regarding User 1 and the location of the impact on the body of User 1. The system of peripheral devices continuously transmits vital sign information for User 1 to one or all members of the team. The application active on the peripheral devices of the team members may also include a feature allowing any member to initiate medical evacuation. The application can also produce an electronic information card (e.g., tactical combat casualty (TCCC) card) that indicates the user status.
Figure 10:
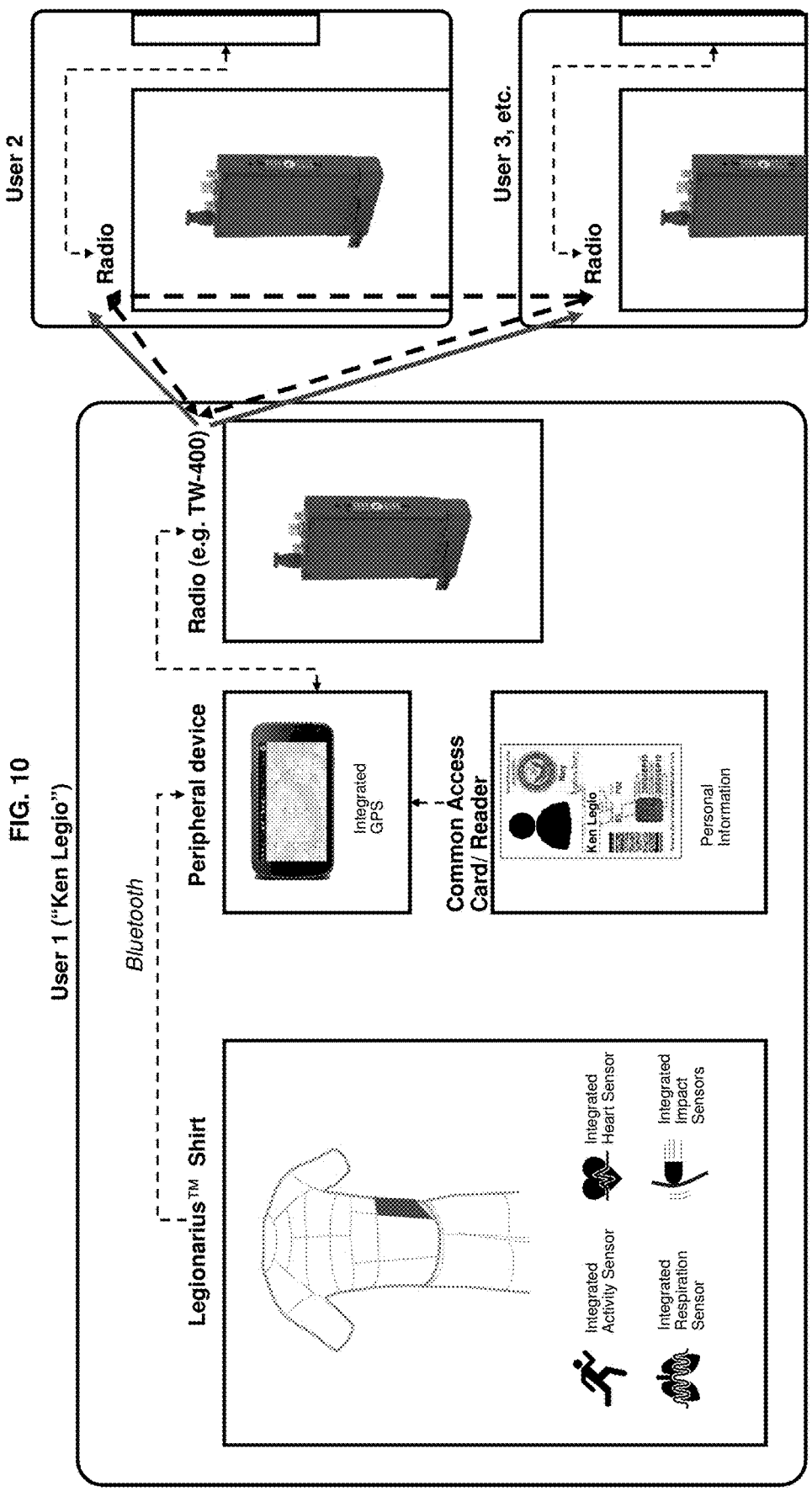
FIG. 10 is a schematic drawing showing a system of the invention which includes a wearable device, a mobile phone running or accessing an application, a common access card reader with personal information, and a radio for external communication to other members of the team ("users"). Once the high velocity impact is detected on User 1, shown as a red panel on the torso of the wearable device, peripheral device transmits information about the VSM sensors, impact location, and user information to the other users. The impact detection may automatically trigger the peripheral device and/or radio to transmit the information to the peripheral devices or radios of other users (red arrows).
Figure 11:
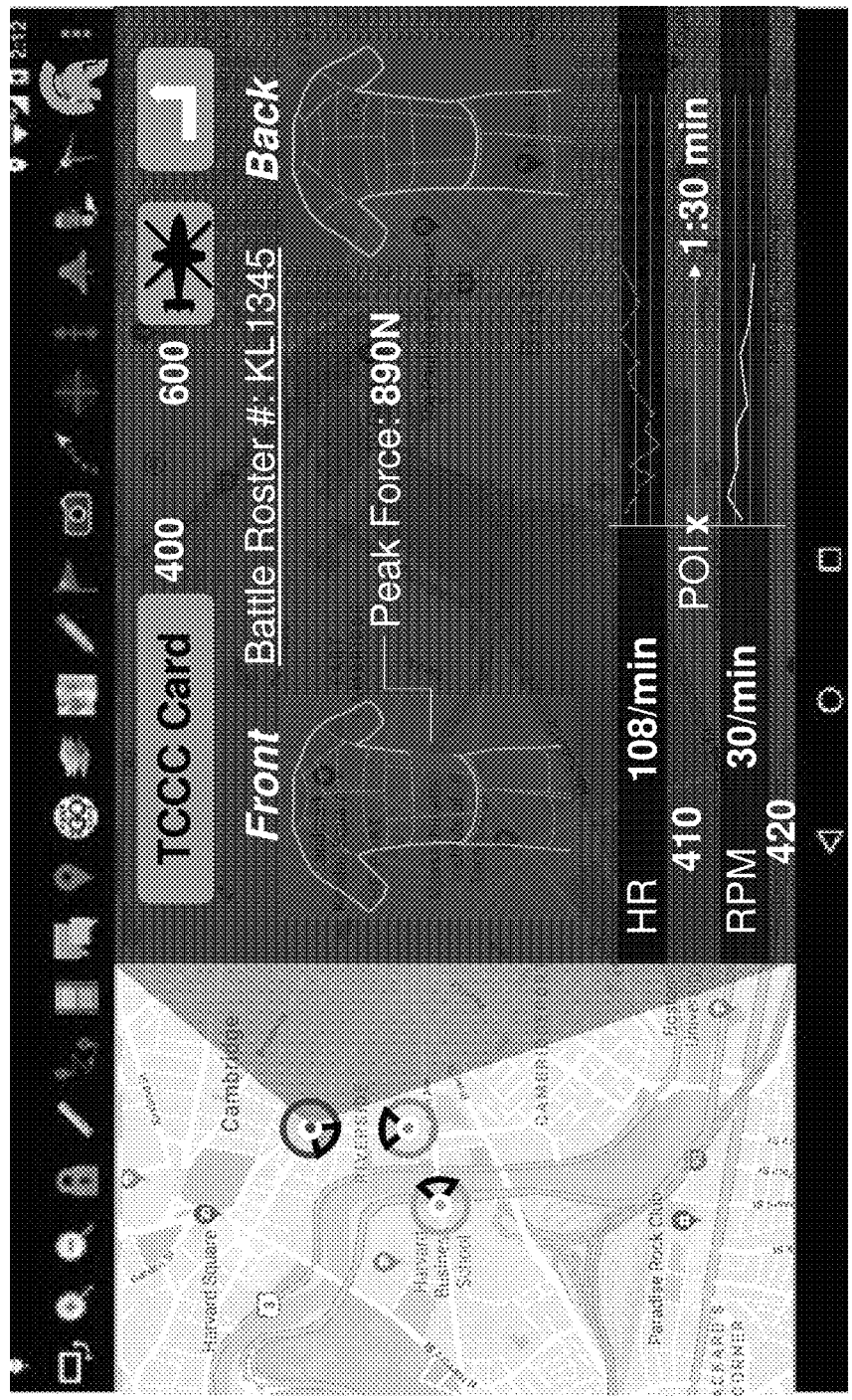
FIG. 11 is a screenshot of a graphical user interface, e.g., that is displayed on a peripheral device. A map displays the position of an injured team member. Each team member can click an icon on the map to open TCCC card 400 corresponding to the injured team member. Information, such as the location and force of the impact, VSM information, and the time of impact (TOI) time stamp are displayed. The graphical user interface also includes icon 600 to initiate a medical evacuation request.

The graphical user interface may display front and rear views of the sensors, e.g., as placed on an avatar of the user (FIGS. 1 and 14) or on an avatar of the equipment, such as a vehicle. When the device senses an impact, the user, via the application on the peripheral device, can then observe when certain sensors are triggered, and an alert message can be transmitted (FIGS. 9-11).

The user of the application may adjust the threshold sensitivity of the sensors or whether they trigger an alert upon activation. For example, a user or equipment (e.g., a vehicle) experiencing a small vibration would not want to trigger an alert message, but upon receipt of a high impact or powerful stimulus, the user would want the stimulus to trigger an alert message. The user may also use differential zone pressure thresholds to vary the sensor threshold in different regions of the wearable device or device on a piece of equipment, e.g., a vehicle. For example, a user may wish to set a higher force threshold (e.g., 15-40 psi, such as 20 psi) for their torso, and a lower force threshold for the head (e.g., 0.5-15 psi, such as 10 psi), such that a lower impact force on the head (or, e.g., the engine, if configured for a vehicle) would trigger a distress signal, but the same impact force on the torso (or, e.g., the bumper, if configured for a vehicle) would not trigger a distress signal. This can also be configured based on the zones of sensors. Additionally, details about the nature and location of the stimulus that triggers activation of the device can be displayed on the graphical user interface. For example, sensors located near a specific part or organ that detect a stimulus would alert the user or a third party responder that a specific organ or location on the body or equipment (e.g., a vehicle) is under duress. Therefore, a first responder would be better prepared upon arrival for treating the injured user or providing maintenance to the equipment (e.g., a vehicle). The user of the device can set certain emergency contacts and the emergency contacts can receive a text or SMS message, or a radio signal (e.g., TW-400) upon triggering of the device (FIG. 10).

Figure 4:
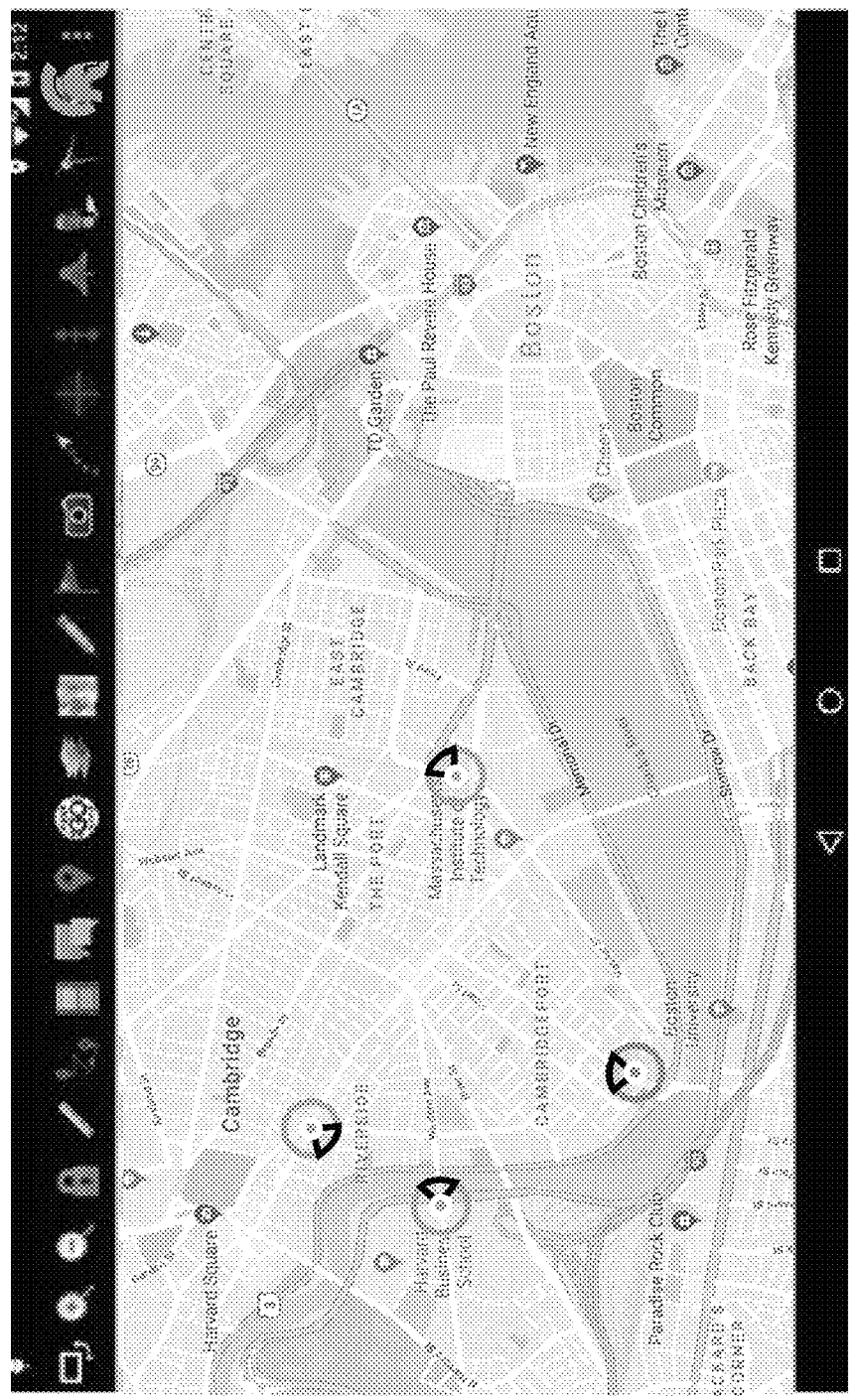
FIG. 4 is a screenshot of a graphical user interface, e.g., that is displayed on a peripheral device. A map displays the position of each member of a team as an encircled dot.
Figure 5:
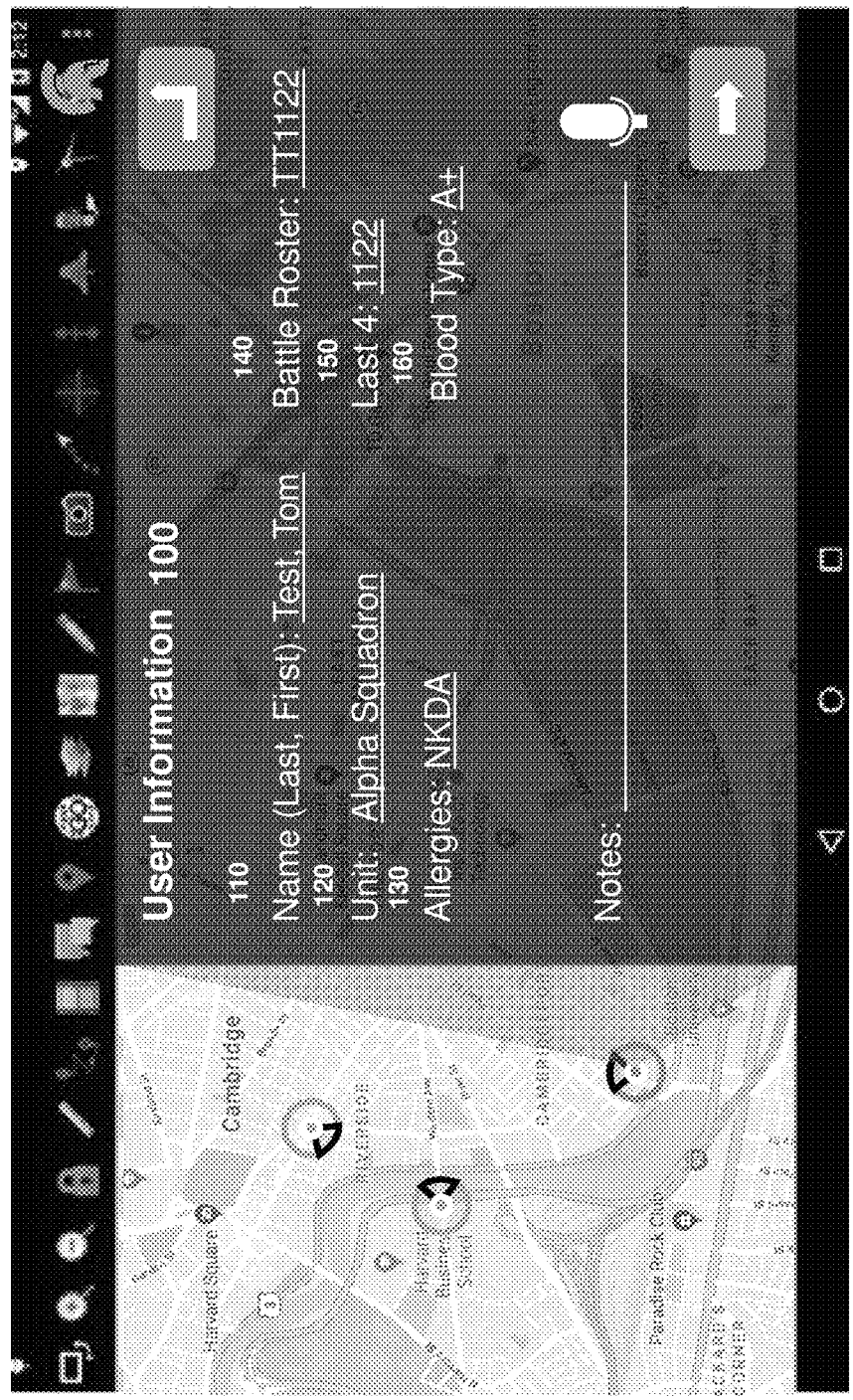
FIG. 5 is a screenshot of a graphical user interface, e.g., that is displayed on a peripheral device. A map displays the position of one member of the team, and user information 100, such as name 110, roster 140, unit 120, allergies 130, last four (e.g., ID number) 150, and blood type 160 are overlayed on a map. When an ID card is scanned at the beginning of a mission (e.g., using a barcode or QR code), the application can automatically loads the various user information in order to personalize the wearable device and system for a specific user.
Figure 6:
FIG. 6 is a screenshot of a graphical user interface, e.g., that is displayed on a peripheral device. The system status 200 is shown, including the power 210, connectivity signal strength 220, the status of the impact sensors 230, and status of the vital signs monitoring (VSM) sensors 240.

FIGS. 4-8 and 11-33 show screenshots of how the application can function and features associated therewith. For example, the application can include a geolocation feature that displays the global position of the user on a map (FIG. 4). The map may also show the position of other users (e.g., team members) using a peripheral device, application, and/or wearable device (e.g., wearable device with one or more, e.g., 2, 3, 4, 5, 6, 7, 8, 9, 10, or more bladders). The application may have a screen that displays user information 100, such as name 110, roster 140, unit 120, allergies 130, last four (e.g., ID number) 150, and blood type 160 (FIG. 5). When an ID card is scanned at the beginning of a mission, the application can automatically load the various user information in order to personalize the wearable device and system for a specific user. The application may have a screen that displays system status 200, such as power 210, connectivity signal 220, and status of the impact 230 and vital signs monitoring (VSM) sensors 240 (FIG. 6).

Figure 7:
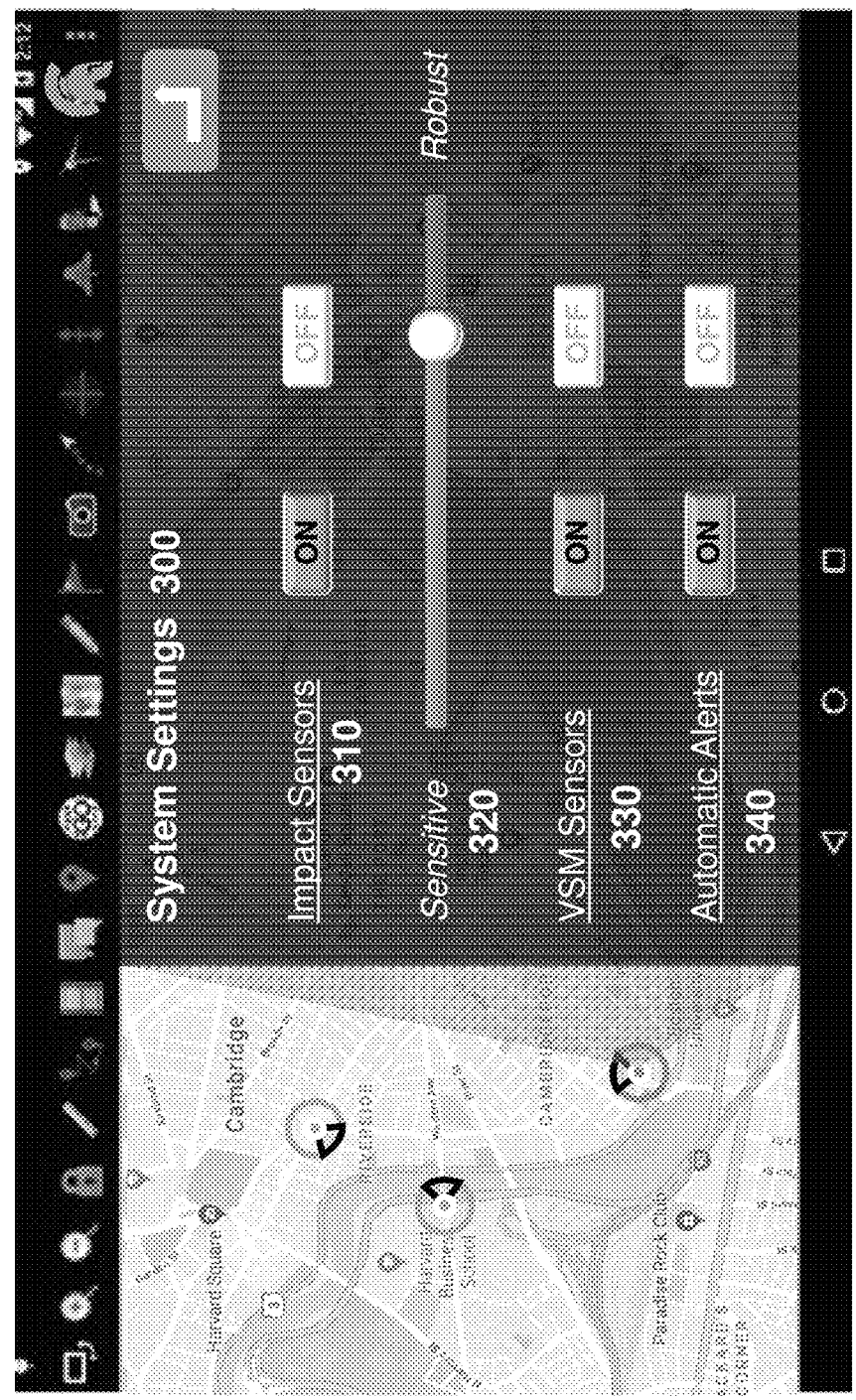
FIG. 7 is a screenshot of a graphical user interface, e.g., that is displayed on a peripheral device. The application allows the user to adjust system settings 300. The impact sensors 310, VSM sensors 330, and automatic alerts 340 can be turned on or off and level of sensitivity 320 of the sensors can be adjusted on a sliding scale.
Figure 8:
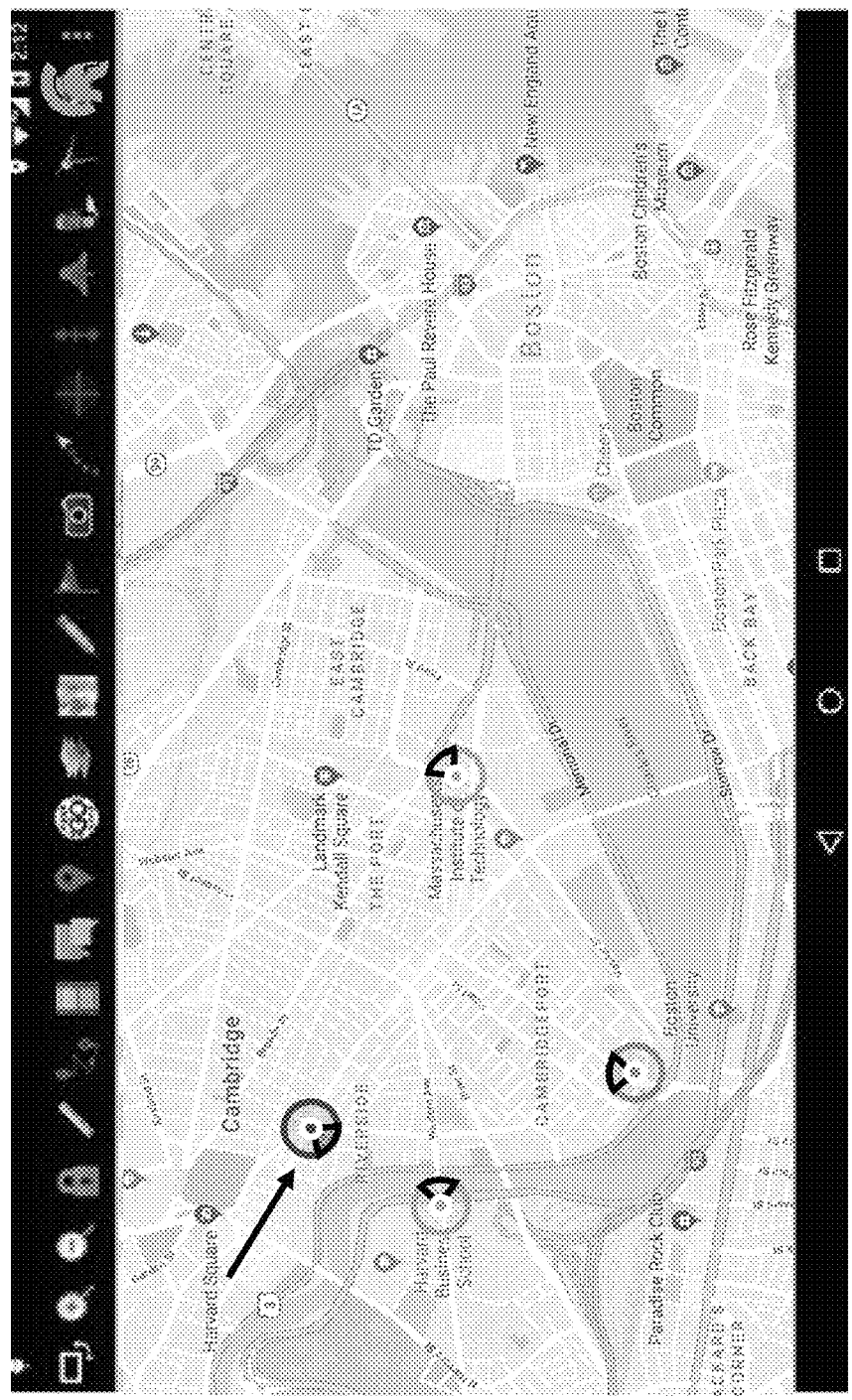
FIG. 8 is a screenshot of a graphical user interface, e.g., that is displayed on a peripheral device. A map displays the position of each member of a team as an encircled dot. In this screenshot, the application shows that a high velocity impact has been detected on User 1 (denoted by the arrow) and the dot changes to a different indicator (e.g., a different color, such as red, or a different icon).

The application may have a screen that displays the system settings 300, which can be adjusted by the user (FIG. 7). The impact sensors 310, VSM sensors 330, and alerts 340 can be turned on or off and the level of sensitivity 320 can be adjusted on a discrete or sliding scale (e.g., from 1 to 10, or from sensitive to robust). The application may include a screen that includes a map that displays the position of each member of a team, e.g., as an encircled dot (FIG. 8). In the event that a high velocity impact is detected on a user, the dot may change to a different indicator, e.g., a color change, such as red, to alert the other team members. (FIG. 8). The components of the system interact with the peripheral device to signal (e.g., via the application or radio) to alert the other team members. One of the other team members may then request a third party responder (e.g., medical evacuation team) if the injury is serious (FIGS. 9-10).

Figure 12:
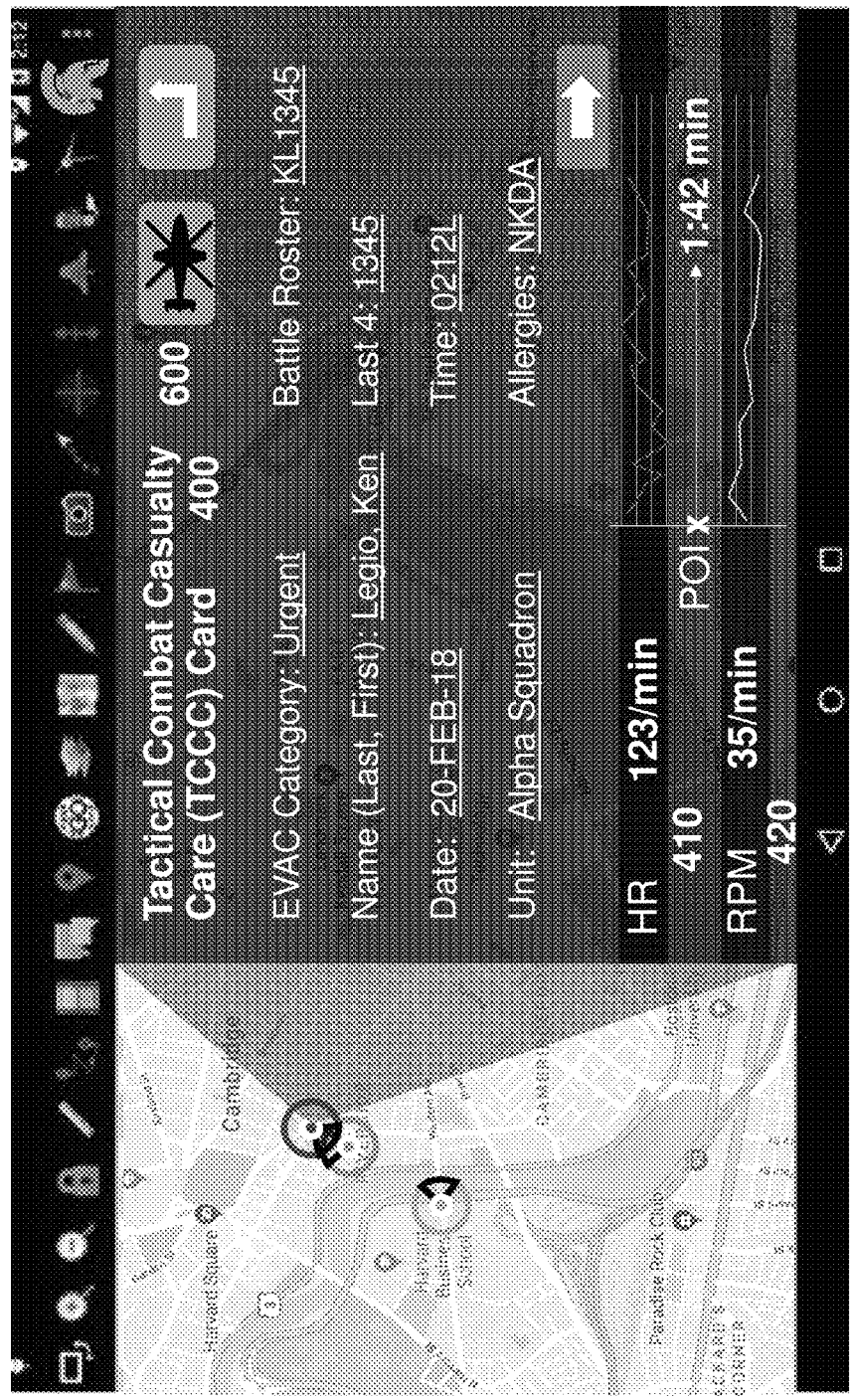
FIG. 12 is a screenshot of a graphical user interface, e.g., that is displayed on a peripheral device. Electronic TCCC card 400 includes various information boxes that are pre-populated, but can be overwritten (e.g., by the injured person or a third party responder), if desired. The bottom part of the screen shows a continuous live transmission view of the injured team member's vital signs, including heart rate 410 and respirations per minute 420.

Once the application running on or accessible from the peripheral device identifies or senses that the user wearing the wearable device has been injured, the application includes multiple features to transmit information specific to the injured user to appropriate personnel. For example, the application may include a screen that shows a map displaying the position of injured user. Each team member can click an icon on the map to open a user information card (e.g., technical combat casualty care (TCCC) card 400) corresponding to the injured team member. Information, such as the location (e.g., arm, torso, and chest) and force (e.g., 10 pN-1000 pN) of the impact, VSM information (e.g., heart rate (beat/min), respiration rate (respirations/min)), and the time or point of impact (TOI/POI) time stamp may be displayed. The application may also include n medical evacuation request icon 600 to initiate a medical evacuation request, e.g., using medical evacuation request form 500. The application may have a screen to input information. This information may be tabulated in an electronic user information card (e.g., electronic TCCC card 400) for easy visual consumption by a third party responder. For example, the application may include a screen with various information boxes that are pre-populated (e.g., evacuation category, name, date, unit, battle roster, ID number (last 4), time, and allergies), but can be overwritten (e.g., by the injured person or a third party responder), if necessary or desired. Additionally, the screen may display a continuous live transmission view of the injured team member's vital signs, such as heart rate 410 and respiration rate 420 (FIG. 12).

Figure 13:
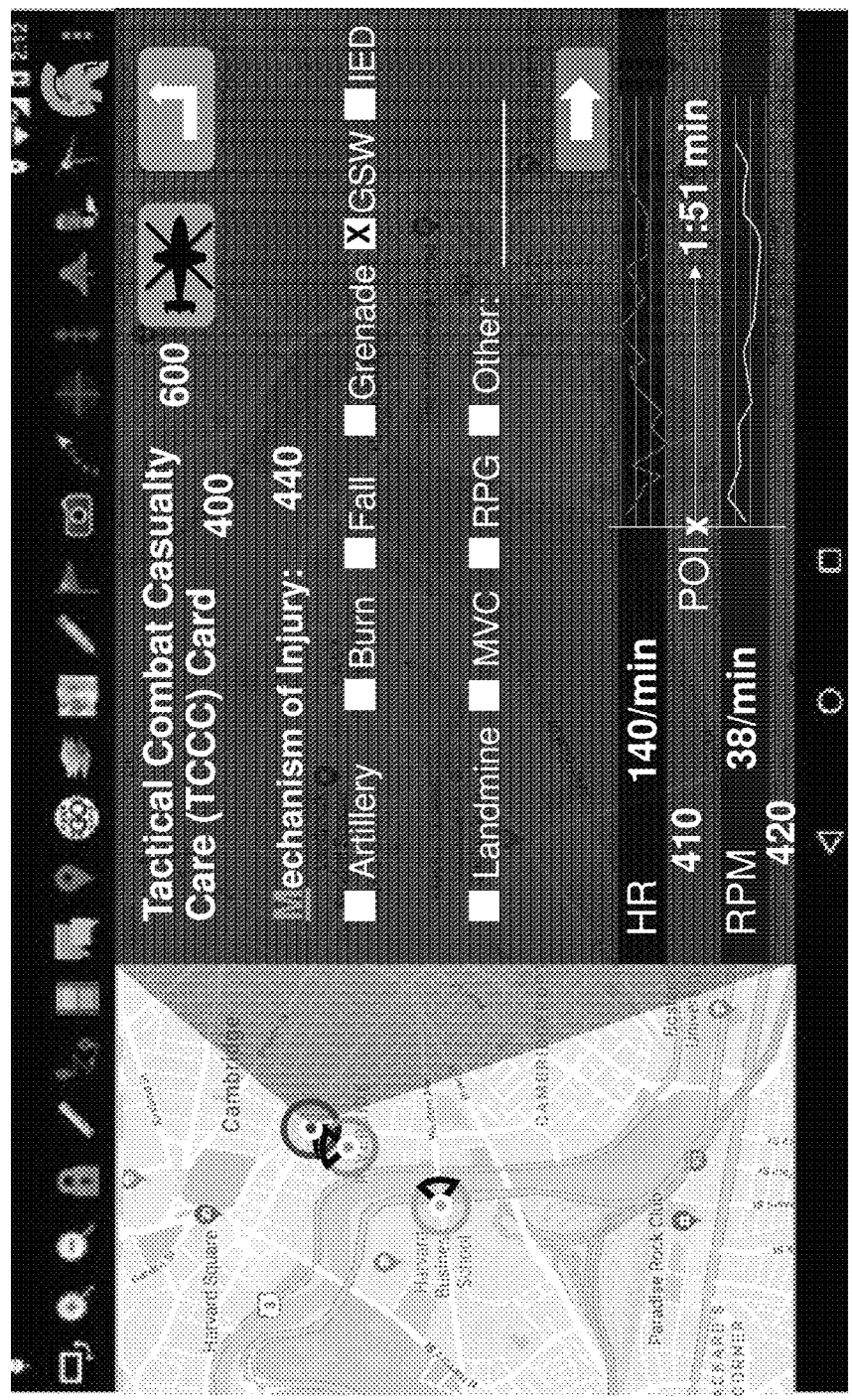
FIG. 13 is a screenshot of a graphical user interface, e.g., that is displayed on a peripheral device. TCCC card 400 includes an input for type or mechanism of injury 440. Shown selected is a gunshot wound.
Figure 14:
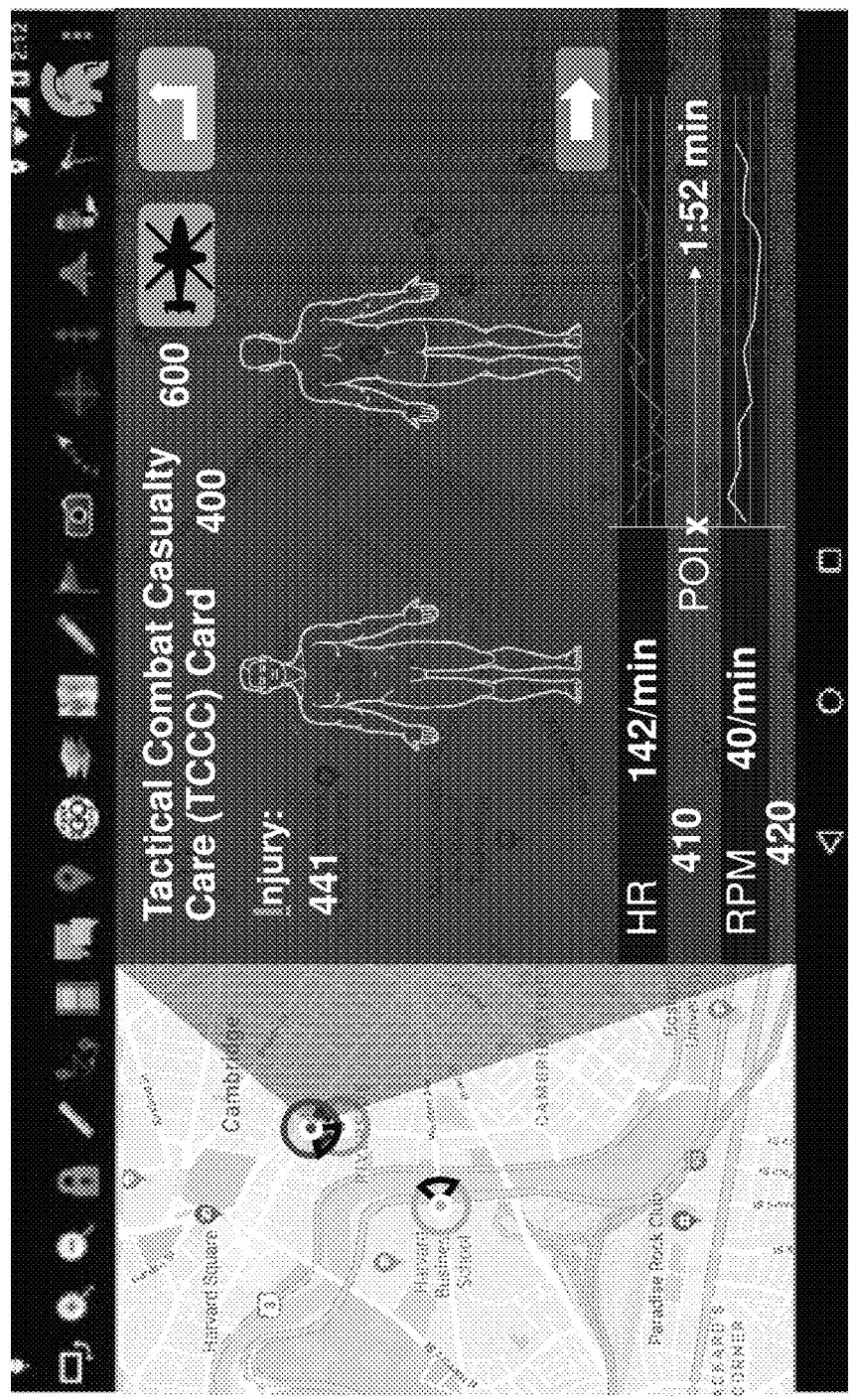
FIG. 14 is a screenshot of a graphical user interface, e.g., that is displayed on a peripheral device. TCCC card 400 shows the location and type of injury 441 on an icon representing the injured team member.
Figure 15:
FIG. 15 is a screenshot of a graphical user interface, e.g., that is displayed on a peripheral device. TCCC card 400 includes an input allowing a user (either an injured user, a team member, or a third party) to specify where on the body (e.g., right or left arm or leg) the injury 442 occurred.
Figure 16:
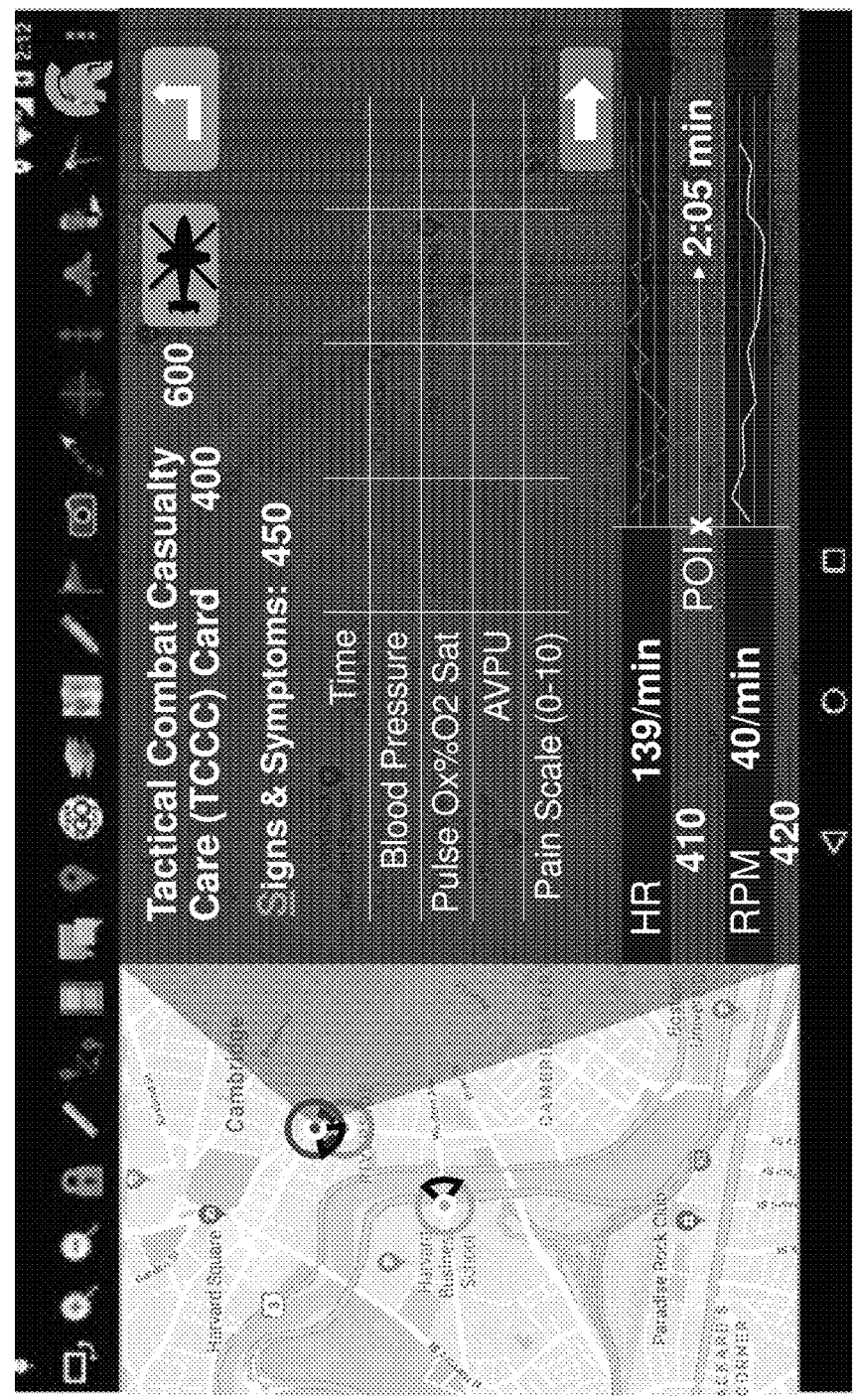
FIG. 16 is a screenshot of a graphical user interface, e.g., that is displayed on a peripheral device. TCCC card 400 includes an input allowing a user (either an injured user, a team member, or a third party) to specify signs and symptoms 450, including time, blood pressure, pulse and oxygen saturation, alert, voice, pain, unresponsive (AVPU), and pain scale (e.g., 1-10).
Figure 17:
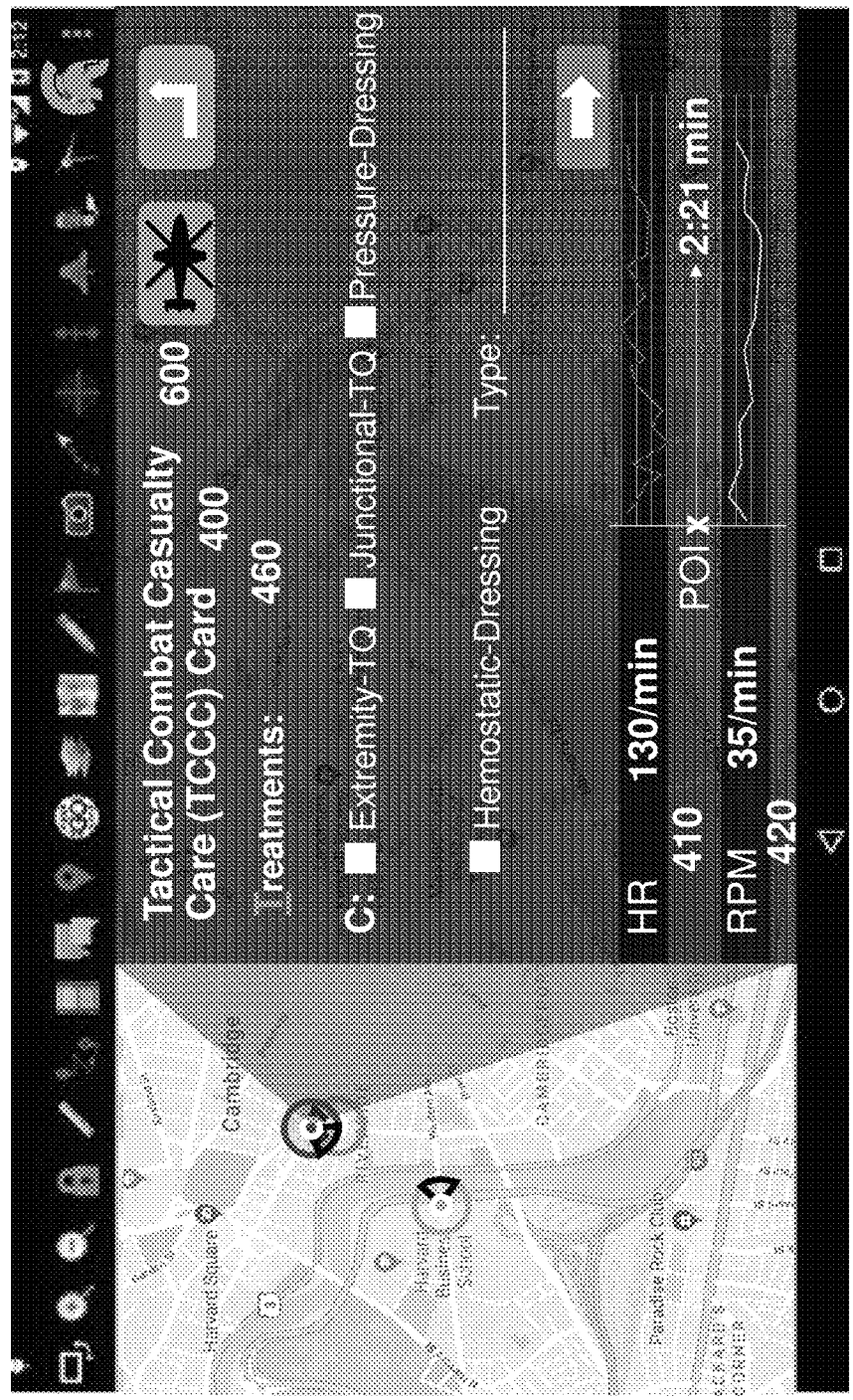
FIG. 17 is a screenshot of a graphical user interface, e.g., that is displayed on a peripheral device. TCCC card 400 includes an input allowing a user (either an injured user, a team member, or a third party) to specify treatment performed 460, such as extremity tourniquet, junctional tourniquet, pressure dressing, or hemostatic dressing.
Figure 18:
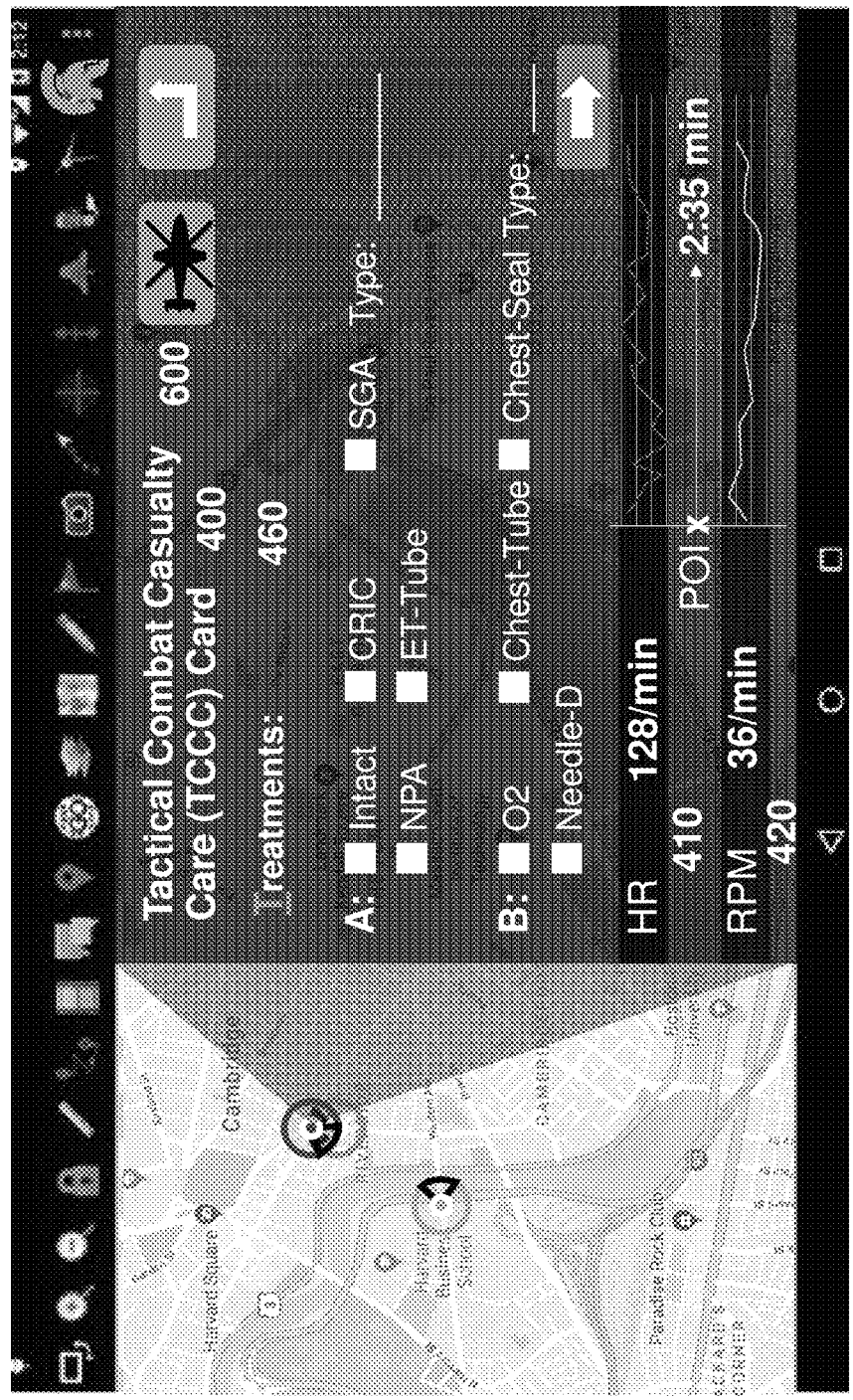
FIG. 18 is a screenshot of a graphical user interface, e.g., that is displayed on a peripheral device. TCCC card 400 includes an input allowing a user (either an injured user, a team member, or a third party) to specify treatment performed 460, such as intact, cricothyrotomy (CRIC), supraglottic airway (SGA), nasopharyngeal airway (NPA), endotracheal tube, oxygen, chest tube, chest seal, or needle.
Figure 19:
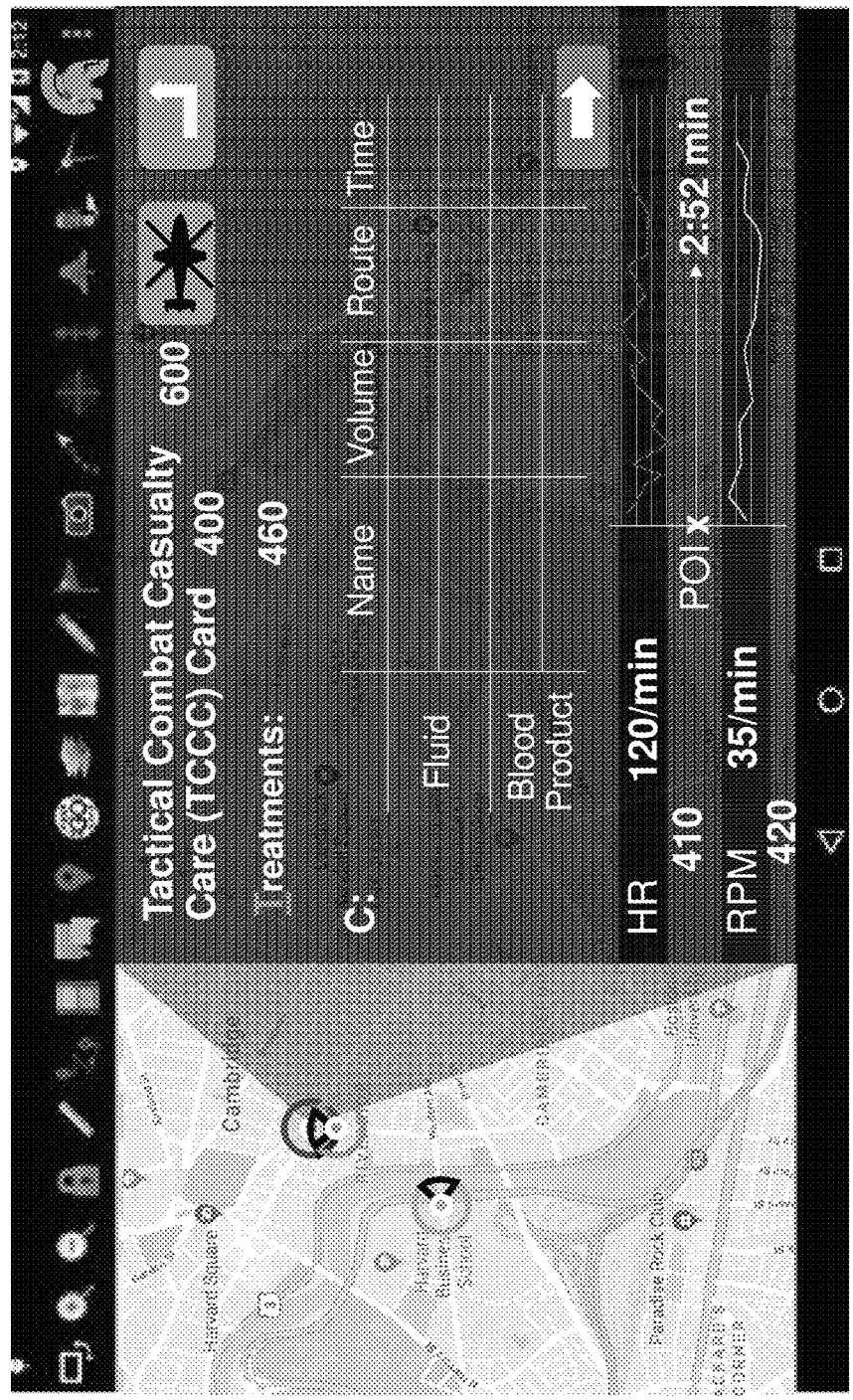
FIG. 19 is a screenshot of a graphical user interface, e.g., that is displayed on a peripheral device. TCCC card 400 includes an input allowing a user (either an injured user, a team member, or a third party) to specify treatment performed 460, such as fluid and blood product, and name, volume, route, and time.
Figure 20:
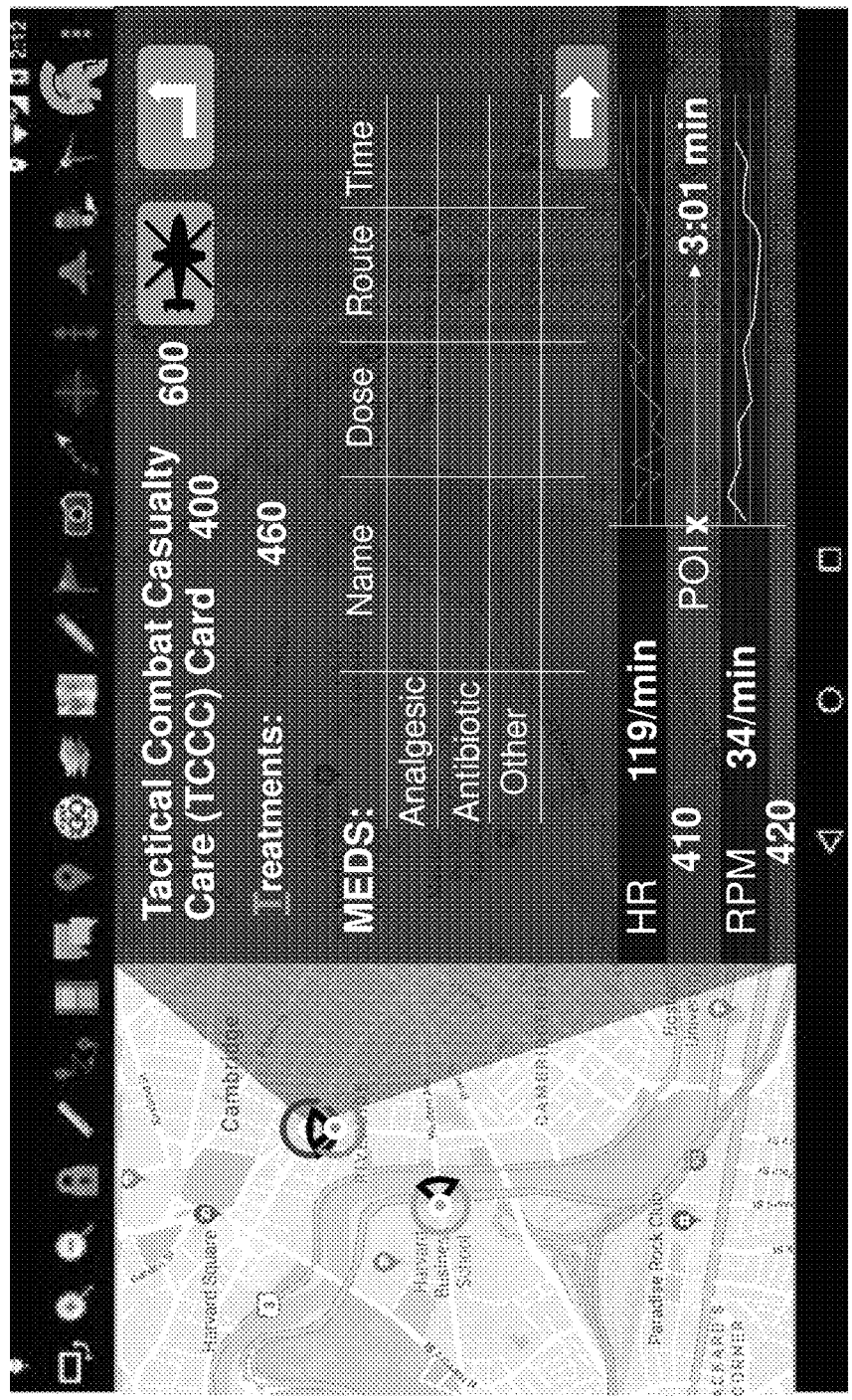
FIG. 20 is a screenshot of a graphical user interface, e.g., that is displayed on a peripheral device. TCCC card 400 includes an input allowing a user (either an injured user, a team member, or a third party) to specify medicines administered 460, such as analgesics, antibiotics, or other, and name, dose, route, and time.
Figure 21:
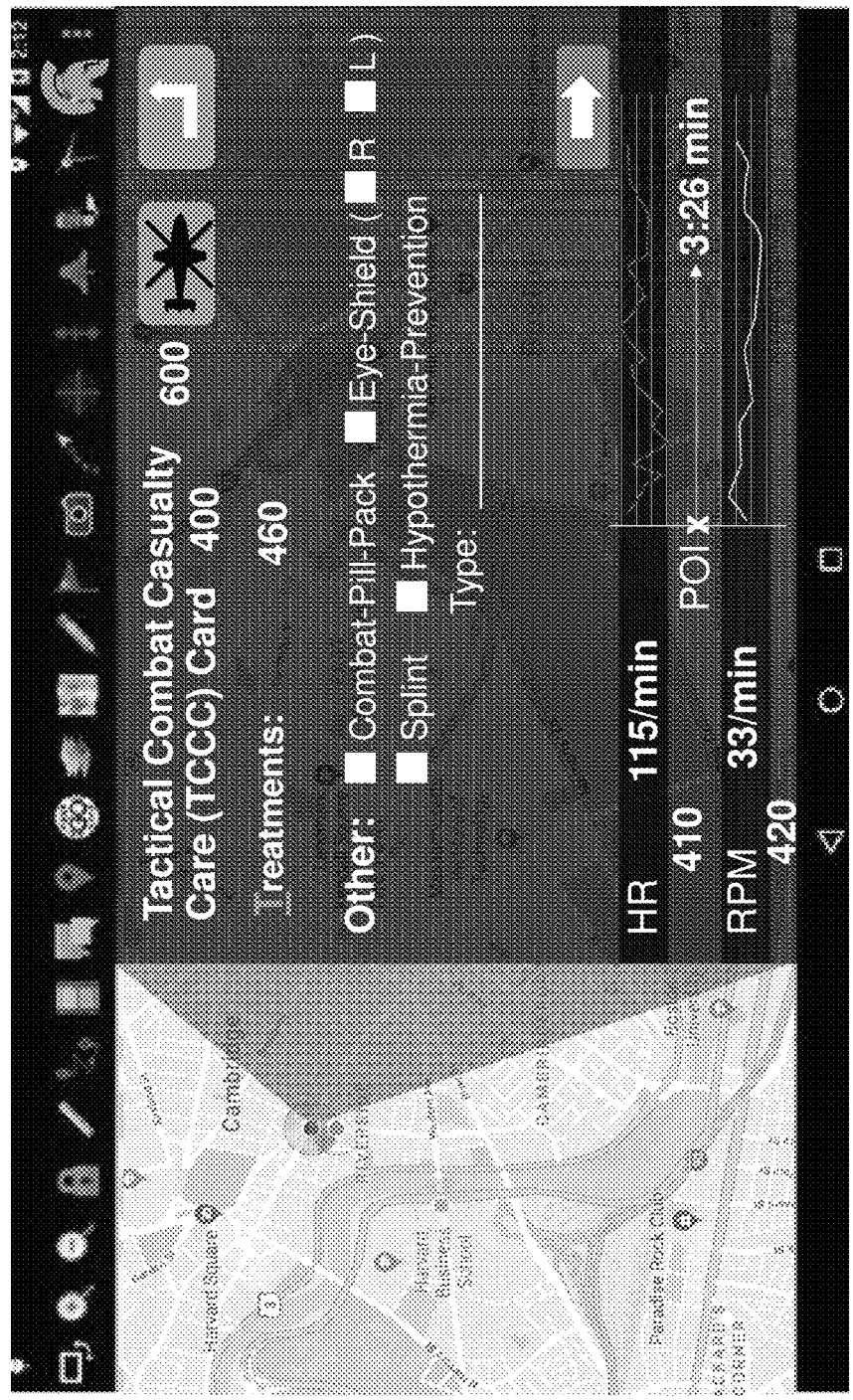
FIG. 21 is a screenshot of a graphical user interface, e.g., that is displayed on a peripheral device. TCCC card 400 includes an input allowing a user (either an injured user, a team member, or a third party) to specify treatments administered 460, such as combat pill pack, eye shield (right or left), splint, or hypothermia prevention.

The application may include a mode to display and/or allow input of a cause of the injury 440 (e.g., artillery, burn, fall, grenade, gunshot wound (GSW), improvised explosive device (IED), landmine, motor vehicle collision (MVC), rocket propelled grenade (RPG), and other) (FIG. 13). The application may include a mode to display and/or allow input of the location and type of injury 441 on the user (FIG. 14). The application may include a mode to display and/or allow input by a user (either the injured user, a team member, or a third party) where on the body (e.g., right, left, arm, or leg) the injury 442 occurred (FIG. 15). The application may include a mode to display and/or allow input of signs and symptoms 450 of the user, including time, blood pressure, pulse and oxygen saturation, alert, voice, pain, unresponsive (AVPU), and pain scale (e.g., 1-10) following an injury (FIG. 16). The application may include a mode to display and/or allow input of a treatment performed 460 (e.g., by a third party responder) on the injured user, such as an extremity tourniquet, junctional tourniquet, pressure dressing, hemostatic dressing (FIG. 17), intact, cricothyrotomy (CRIC), supraglottic airway (SGA), nasopharyngeal airway (NPA), endotracheal tube, oxygen, chest tube, chest seal, or needle (FIG. 18). The application may include a mode to display and/or allow input of a blood treatment performed on the injured user, such as fluid and blood product, and name, volume, route, and time (FIG. 19). The application may also include a mode to display and/or allow input of medicines administered to the injured user, such as analgesics, antibiotics, or other, and name, dose, route, and time (FIG. 20), and/or treatments administered, such as combat pill pack, eye shield (e.g., right or left), splint, or hypothermia prevention (FIG. 21). The application may further include a mode to display and/or allow input of additional notes.

Figure 22:
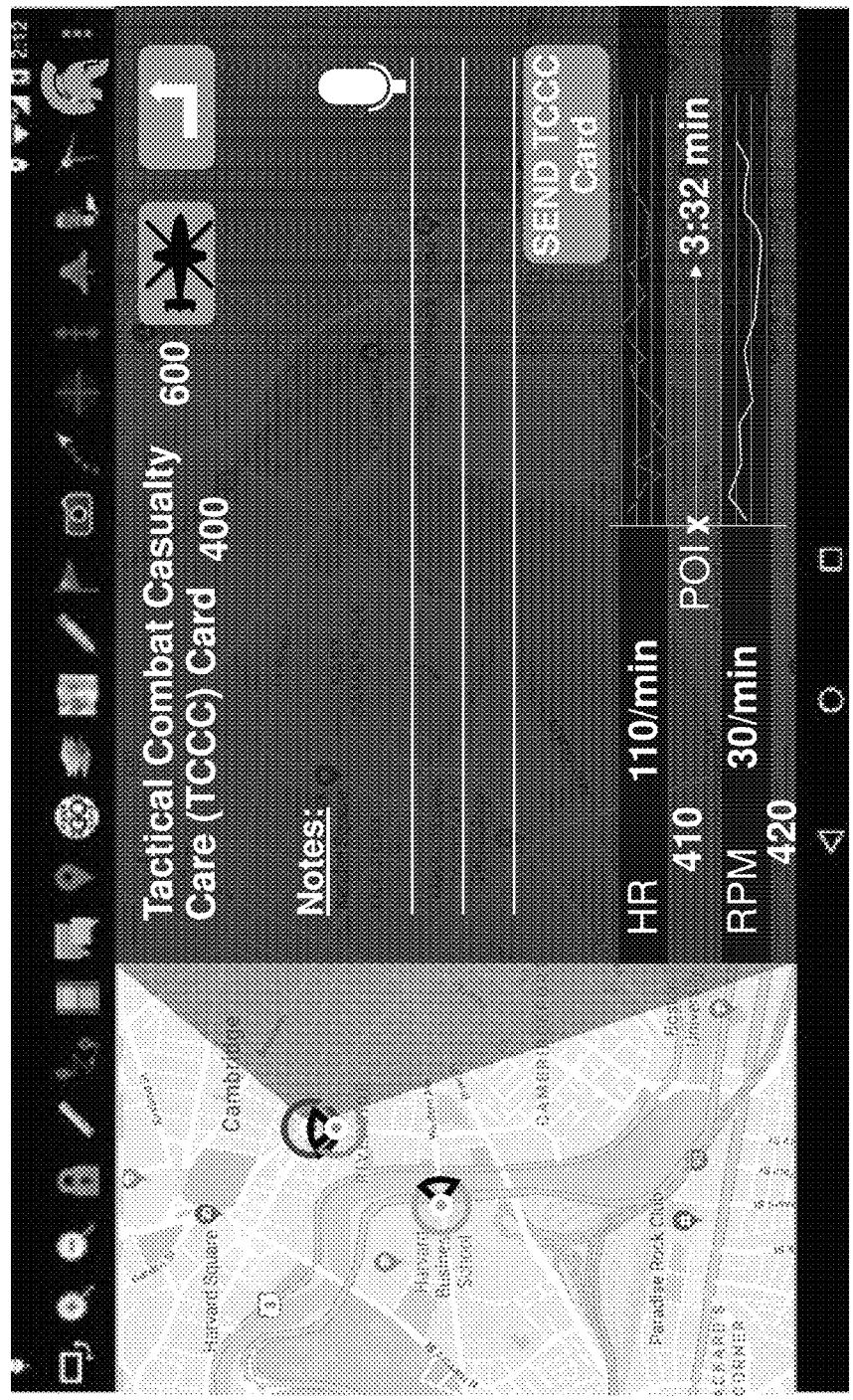
FIG. 22 is a screenshot of a graphical user interface, e.g., that is displayed on a peripheral device. TCCC card 400 includes an entry for additional notes. Once the information is filled out on TCCC card 400, the injured user, a team member, or a third party responder can request medical evacuation and/or send TCCC card 400 to another responder, team members, or a medical evacuation team.
Figure 23:
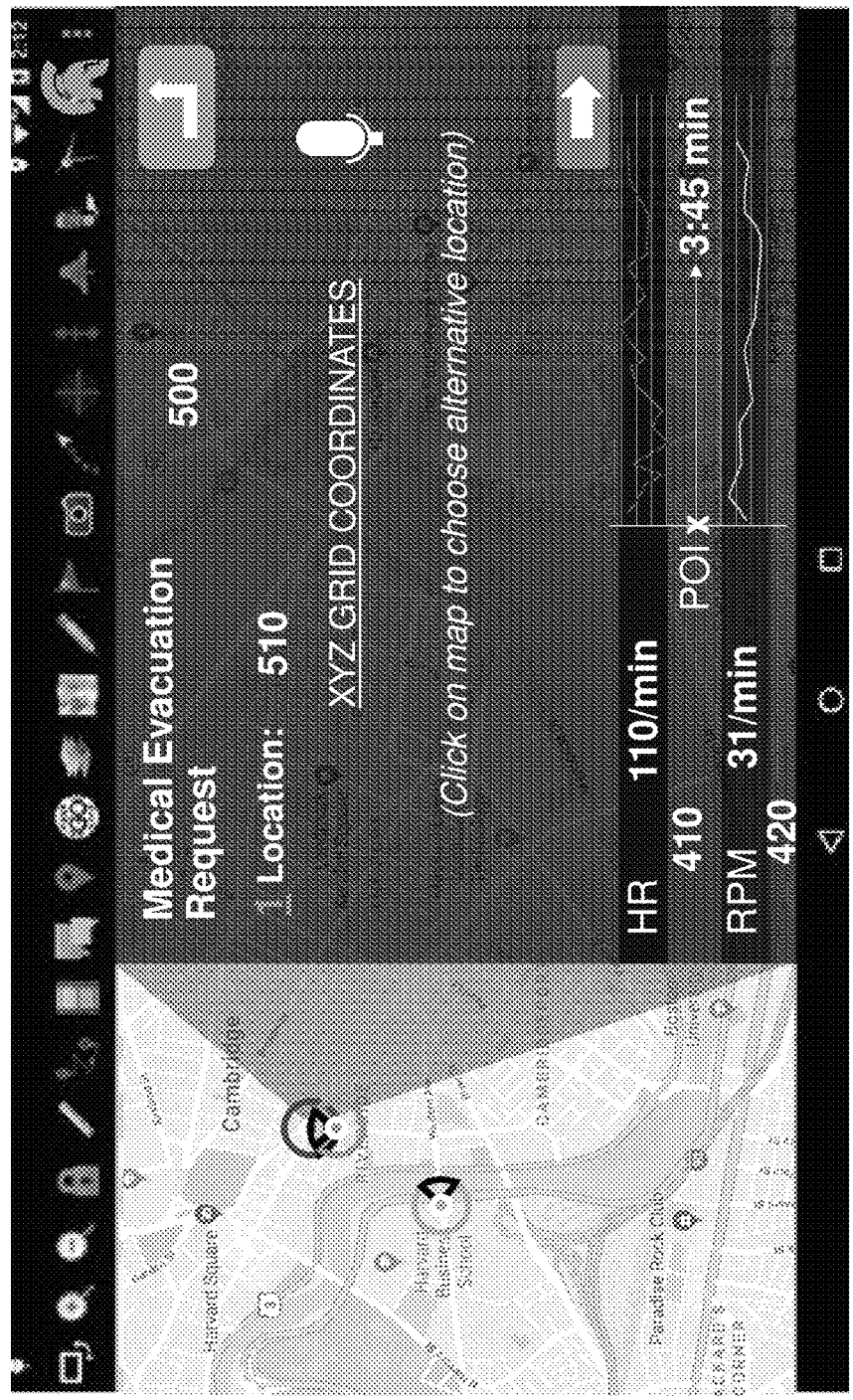
FIG. 23 is a screenshot of a graphical user interface, e.g., that is displayed on a peripheral device. A user of the device can request medical evacuation using medical evacuation request form 500 and can input location 510 (e.g., GPS location) by selecting the XYZ grid coordinates on a map.
Figure 24:
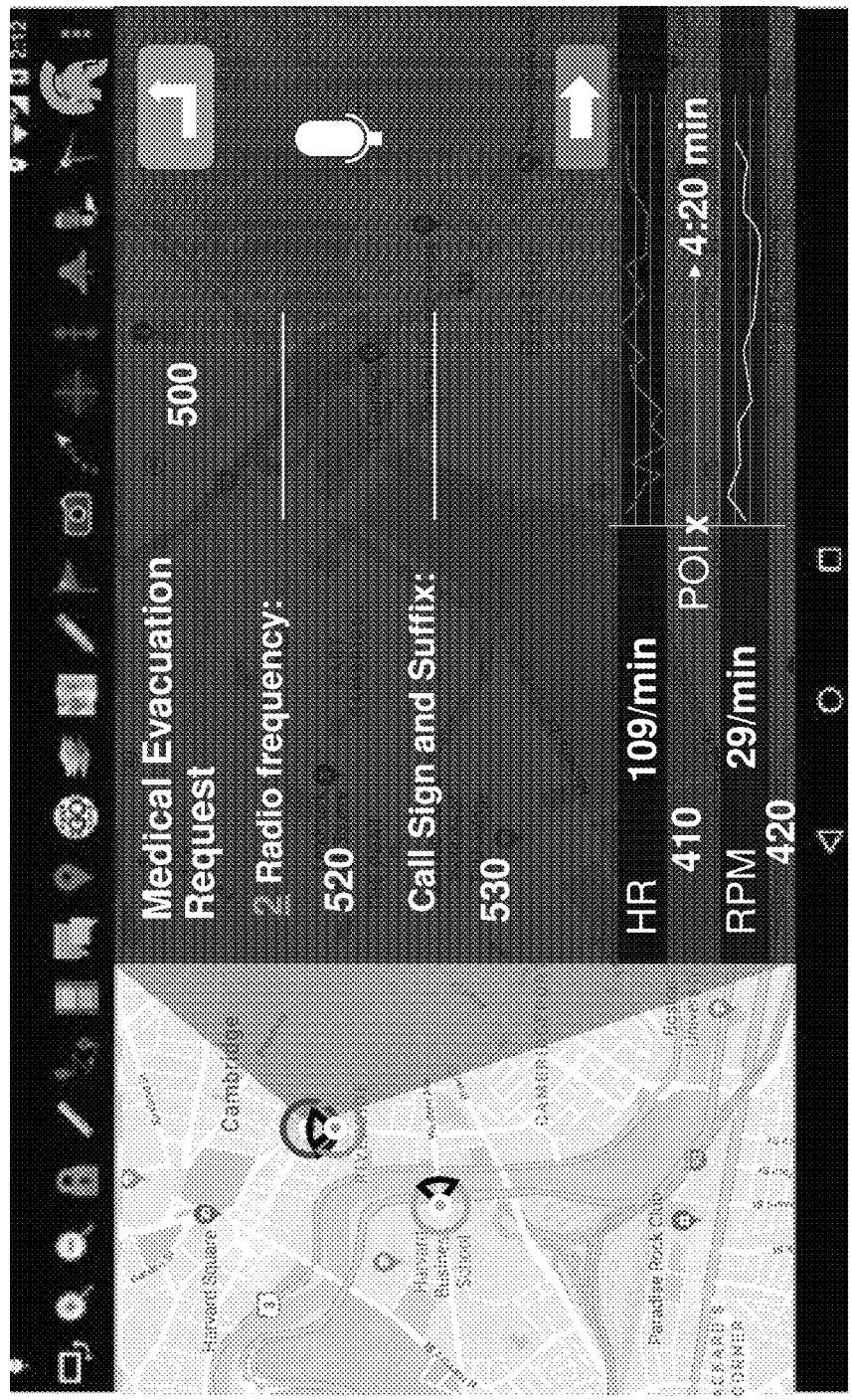
FIG. 24 is a screenshot of a graphical user interface, e.g., that is displayed on a peripheral device. The user requesting medical evacuation can input indicia into the application, such as specific radio frequency 520, call sign and suffix 530 identifying the user, for dissemination to another team member or a third party responder.
Figure 25:
FIG. 25 is a screenshot of a graphical user interface, e.g., that is displayed on a peripheral device. The user requesting medical evacuation can indicate the number of patients (PXT) by precedence 540 (e.g., urgent, urgent-surgery required, priority, routine, and convenience).
Figure 26:
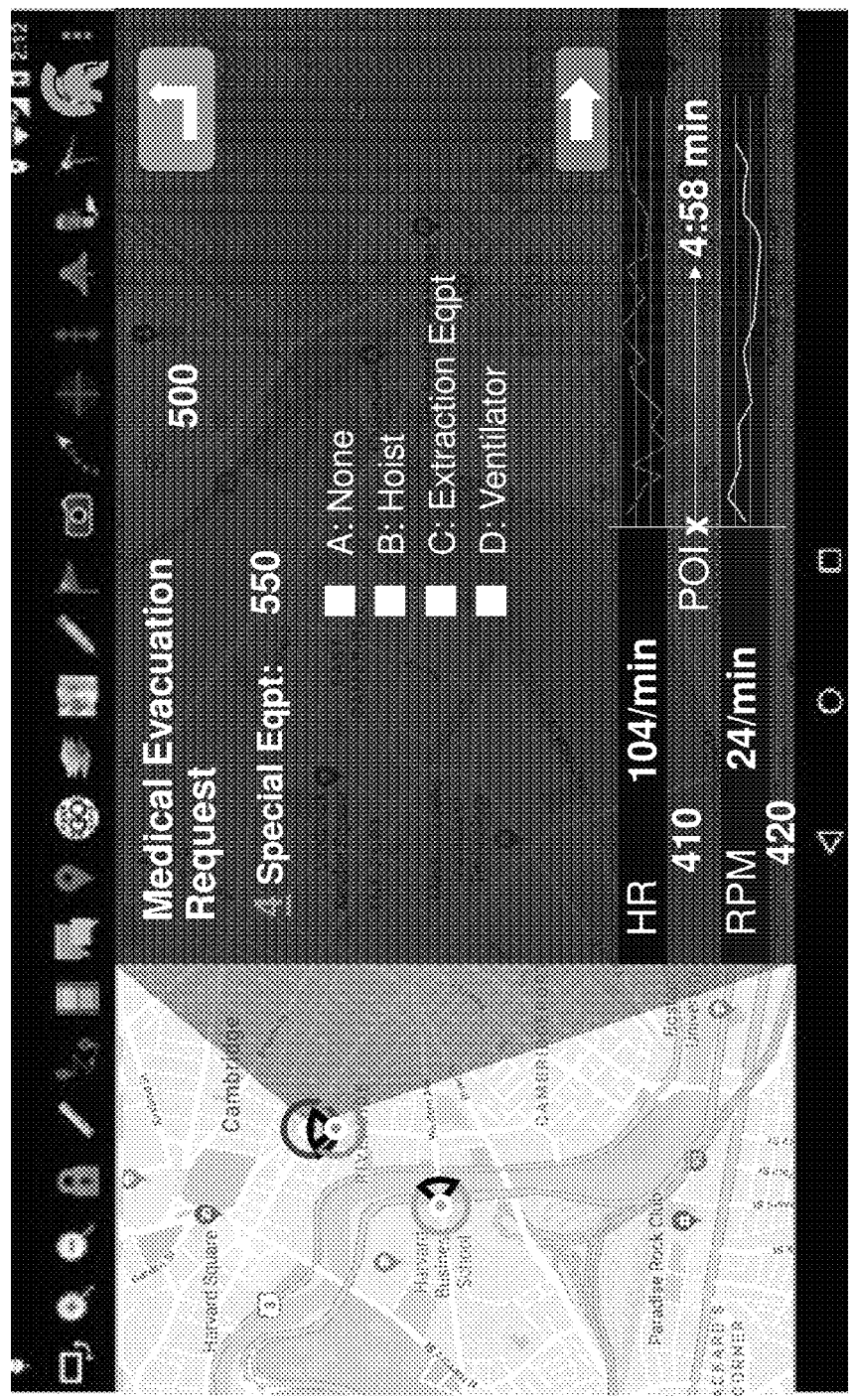
FIG. 26 is a screenshot of a graphical user interface, e.g., that is displayed on a peripheral device. The user requesting medical evacuation can request special equipment 550, such as a hoist, extraction equipment, or a ventilator.
Figure 27:
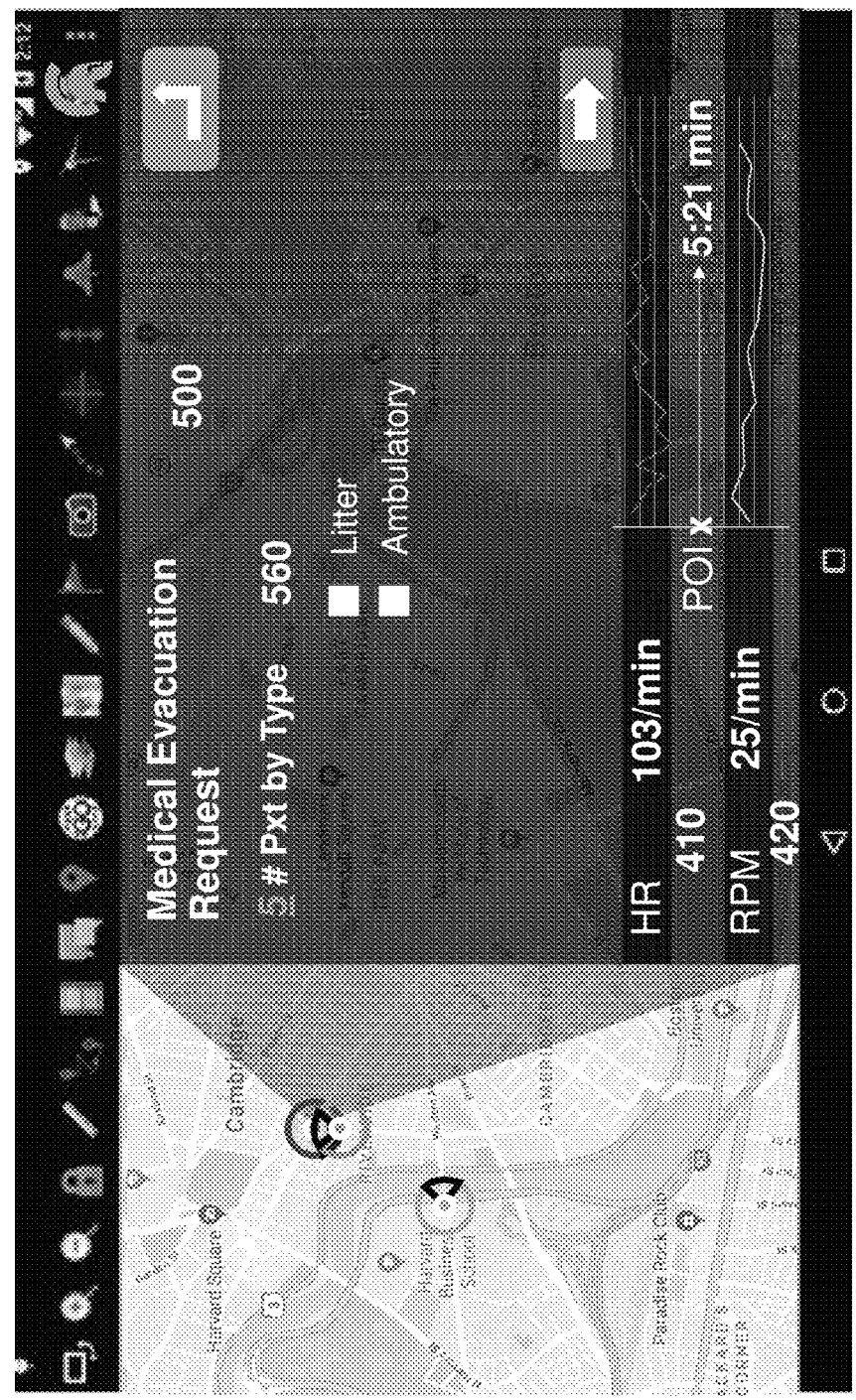
FIG. 27 is a screenshot of a graphical user interface, e.g., that is displayed on a peripheral device. The user requesting medical evacuation can indicate the number of patients (PXT) by type 560 (e.g., litter and ambulatory).
Figure 28:
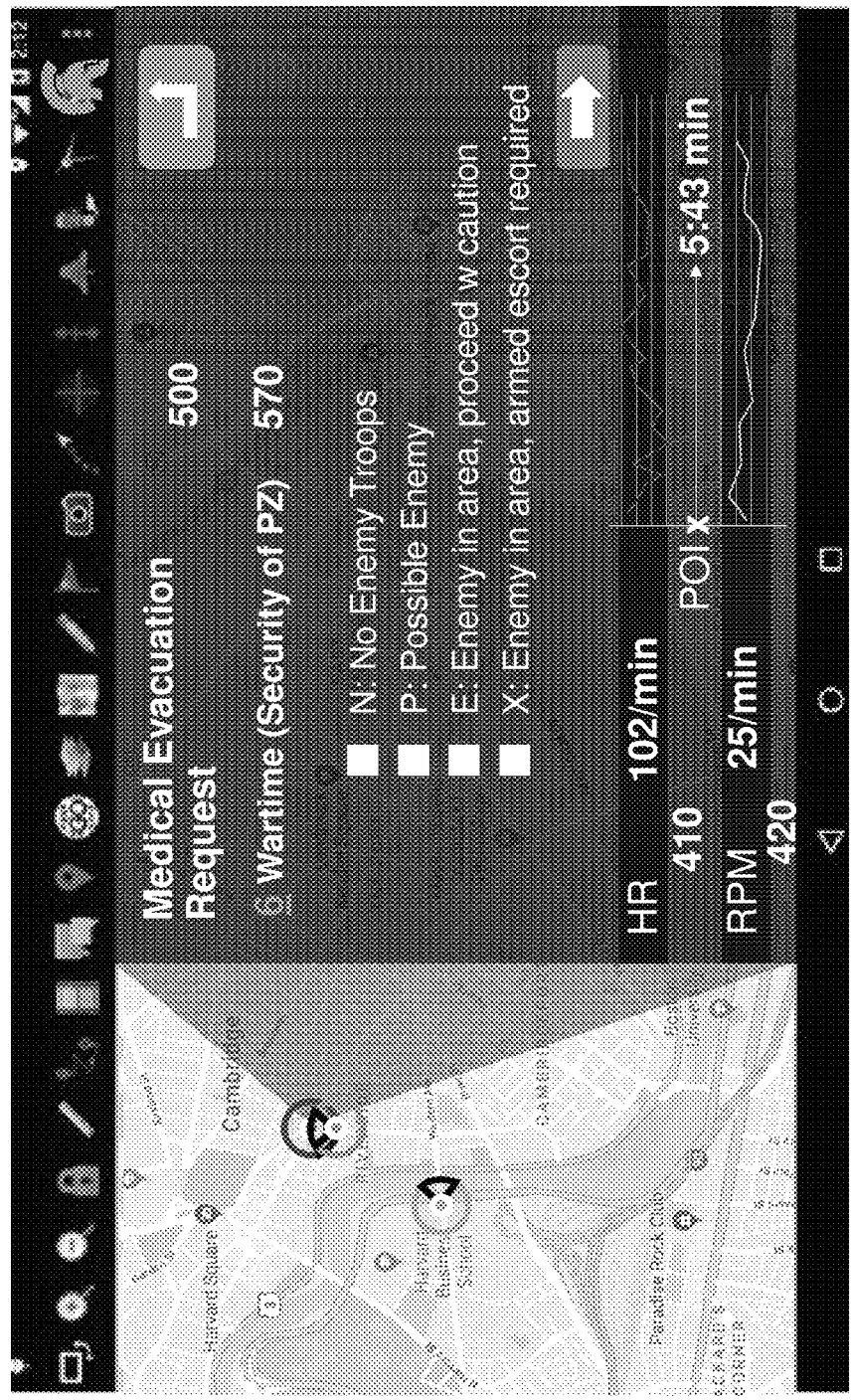
FIG. 28 is a screenshot of a graphical user interface, e.g., that is displayed on a peripheral device. The user requesting medical evacuation can indicate wartime security 570 of the patient zone (e.g., no enemy troops, possible enemy, enemy in area/proceed with caution, and enemy in area/armed escort required).
Figure 29:
FIG. 29 is a screenshot of a graphical user interface, e.g., that is displayed on a peripheral device. The user requesting medical evacuation can indicate method of site marking 580 (e.g., panels, pyrotechnic signal, smoke signal, and no signal).
Figure 30:
FIG. 30 is a screenshot of a graphical user interface, e.g., that is displayed on a peripheral device. The user requesting medical evacuation can indicate patient nationality and status 590 (e.g., US military, US civilian, non-US military, non-US civilian, and enemy prisoner of war (EPW)).
Figure 31:
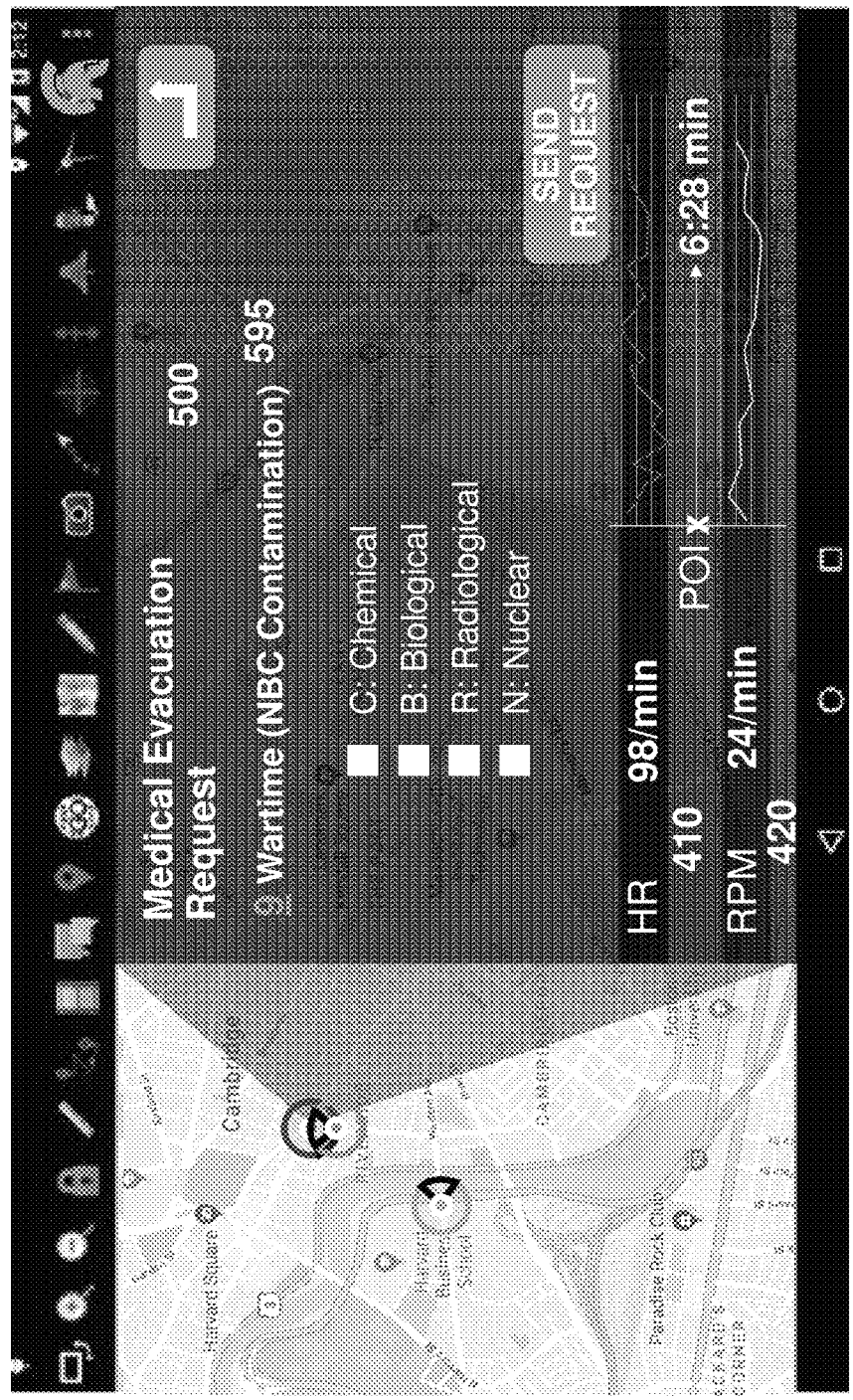
FIG. 31 is a screenshot of a graphical user interface, e.g., that is displayed on a peripheral device. The user requesting medical evacuation can indicate wartime nuclear, biological, or chemical (NBC) contamination status 595 (e.g., chemical, biological, radiological, and nuclear).

Once the information is filled out using the application, the application provides further functionality allowing the injured user or a third party responder to request medical evacuation and/or to send the user information card (e.g., an electronic TCCC card) to another responder or medical evacuation team (FIG. 22). If the user or a responder determines that a medical evacuation is required, the user can input location 510 (e.g., GPS location) by selecting, e.g., XYZ grid coordinates on a map (FIG. 23). The user requesting medical evacuation can also input a specific radio frequency 520 and call sign and suffix 530 that he is using (FIG. 24) and indicate number of injured users or others, e.g., patients (PXT) by precedence 540, (e.g., urgent, urgent-surgery required, priority, routine, and convenience) (FIG. 25). Furthermore, the application includes programming to allow the user to request special equipment 550, such as a hoist, extraction equipment, or a ventilator (FIG. 26). The application may include an entry to indicate the number of inured users or others, e.g., patients (PXT) by type 560 (e.g., litter and ambulatory) (FIG. 27). The application may also include a feature to indicate the wartime security 570 of the user zone (e.g., no enemy troops, possible enemy, enemy in area/proceed with caution, and enemy in area/armed escort required) (FIG. 28). The application may also include a feature to indicate method of marking 580 (e.g., panels, pyrotechnic signal, smoke signal, or no signal) (FIG. 29). The user requesting medical evacuation can indicate nationality and status 590 (e.g., US military, US civilian, non-US military, non-US civilian, and enemy prisoner of war (EPW)) of an injured user or other personnel (FIG. 30). Additionally, the user requesting medical evacuation may indicate the wartime nuclear, biological, or chemical (NBC) contamination status 595 (e.g., chemical, biological, radiological, and nuclear) (FIG. 31). If using, e.g., an ATAK platform and a TCCC card, the application can process all of the sensor data and the information inputted and/or gathered via the graphical user interface onto an electronic TCCC card to summarize all of the information for a third party responder (FIG. 32). If not using an ATAK platform, the application can process all of the sensor data and the information inputted and/or gathered via the graphical user interface onto a user information card (e.g., electronic user information card). The application may also output the data onto a medical evacuation request form to summarize all of the information for a third party responder. An exemplary medical evacuation request form is shown in Table 1 below.

TABLE 1

Medical Evacuation Request Form

| LINE | ITEM | EXPLANATION | WHERE/HOW OBTAINED | WHO NORMALLY PROVIDES | REASON |
| --- | --- | --- | --- | --- | --- |
| 1 | Location of pickup site | Encrypt the grid coordinates of the pickup site. When using the DRYAD Numeral Cipher, the same "SET" line will be used to encrypt the grid zone letters and the coordinates. To preclude misunderstanding, a statement is made that grid zone letters are included in the message (unless unit SOP specifies its use at all times). | From map | Unit leader(s) | Required so evacuation vehicle knows where to pick up patient. Also, so that the unit coordinating the evacuation mission can plan the route for the evacuation vehicle (if the evacuation vehicle must pick up from more than one location). |
| 2 | Radio frequency, call sign, and suffix | Encrypt the frequency of the radio at the pickup site, not a relay frequency. The call sign (and suffix if used) of person to be contacted at the pickup site may be transmitted in the clear. | From SOI | RTO | Required so that evacuation vehicle can contact requesting unit while en route (obtain additional information or change in situation or directions). |
| 3 | Number of patients by precedence | Report only applicable information and encrypt the brevity codes.<br>A - URGENT<br>B - URGENT-SURG<br>C - PRIORITY<br>D - ROUTINE<br>E - CONVENIENCE<br>If two or more categories must be reported in the same request, insert the word "BREAK" between each category. | From evaluation of patient(s) | Medic or senior person present | Required by unit controlling vehicles to assist in prioritizing missions. |
| 4 | Special equipment required | Encrypt the applicable brevity codes.<br>A - None<br>B - Hoist<br>C - Extraction equipment<br>D - Ventilator | From evaluation of patient/situation | Medic or senior person present | Required so that the equipment can be placed on board the evacuation vehicle prior to the start of the mission. |

TABLE 1-continued

Medical Evacuation Request Form

| LINE | ITEM | EXPLANATION | WHERE/HOW OBTAINED | WHO NORMALLY PROVIDES | REASON |
|---|---|---|---|---|---|
| 5 | Number of patients by type | Report only applicable information and encrypt the brevity code. If requesting medical evacuation for both types, insert the word "BREAK" between the litter entry and ambulatory entry.<br>L + # of patients - Litter<br>A + # of patients - Ambulatory (sitting) | From evaluation of patient(s) | Medic or senior person present | Required so that the appropriate number of evacuation vehicles may be dispatched to the pickup site. They should be configured to carry the patients requiring evacuation. |
| 6 | Security of pickup site (wartime) | N - No enemy troops in area<br>P - Possibly enemy troops in area (approach with caution)<br>E - Enemy troops in area (approach with caution)<br>X - Enemy troops in area (armed escort required) | From evaluation of situation | Unit leader | Required to assist the evacuation crew in assessing the situation and determining if assistance is required. More definitive guidance can be furnished the evacuation vehicle while it is en route (specific location of enemy to assist an aircraft in planning its approach). |

Graphical User Interface

The peripheral devices described herein include a graphical user interface that displays various sensor information and health indicia associated with a user wearing the wearable device or operational status of a device configured for use with a piece of equipment, such as a vehicle. The sensor information and health indicia is collected by the sensors, e.g., on the wearable device or equipment device (e.g., vehicle), and processed by the application. The application outputs the information to the graphical user interface. The application can be configured to output information regarding the status of the device (e.g., the wearable device or the equipment/device), such as stored energy level or remaining battery power or on/off status. The application can also output data to the graphical user interface regarding information about the features or stimuli detected by the sensors of the wearable device. The graphical user interface may be an LED device or other monitor, tablet, or smartphone, or the like, as long as it is capable of displaying or depicting information to a user. The graphical user interface may be connected (e.g., wired, or wirelessly) to the wearable device, equipment (e.g., a vehicle), or to the peripheral device. The graphical user interface may be connected to a central information processing unit of the wearable device or equipment. The graphical user interface may be affixed on the wearable device or equipment, for example, on the arm, torso, or belt region of the wearable device, or on the equipment (e.g., a vehicle). Alternatively, the graphical user interface may be integrated into the materials of the device or affixed on top of the outer layer of the device. The graphical user interface may be the peripheral device or part of the peripheral device.

Information Processing Unit

The peripheral device and/or the wearable device includes an information processing unit. The information processing unit may include one or more of a processor, controller, a programmable memory, and/or a data storage system (e.g., a flash memory system) which can be used to record data from sensor inputs. The unit processes the signals received from the impact detection and other sensors (if incorporated), such as vital signs monitoring (VSM) sensors, temperature sensors, moisture sensors, and pressure sensors. Depending on the outcome of the computation in interaction with the program stored on the memory, the unit may then alert a third party responder (e.g., medical responder or team member, or a mechanic). Furthermore, the unit may transmit a signal to activate the wearable device to treat the injured subject, e.g., by inflating bladders in the region wherein the injury was detected. The unit may also determine the need to inflate certain other areas, (e.g., in order to provide for an increase of buoyancy forces to keep a user afloat that was injured while in or by the water). The information processing unit may also trigger the transmission of data (such as a distress signal) via a data transmission unit. The information processing unit may be incorporated into the peripheral device and programmed to interact with the application or vice versa. The information processing unit may be a smartphone (e.g., ANDROID™). Alternatively, the information processing unit may be part of a cloud-based or internet-based system (e.g., a remote server).

The information processing unit may be configured to identify the nature (e.g., directionality or force) of the impact or wound by analyzing sensor data. For example, by sensing the pressure at an impact area, the information processing unit can quantify the mass, velocity, and size of a projectile hitting the wearable device. Furthermore, the information processing unit can be configured to identify where the projectile enters and/or exits the wearable device or equipment (e.g., a vehicle), and, thus, the relative entry and/or exit wounds on the body of the user or equipment (e.g., a vehicle). By coupling this data with the specific location on the device where the impact occurs, indicia is provided that can alert the user and/or a third party responder as to the identity, nature, and severity of the wound to the user or the damage to or destruction of the equipment.

The information processing unit may be configured to integrate data obtained from multiple different types of sensors to provide essential physiological information about the health status of a user or the operational status of equipment. By integrating various sensor data, the information processing unit provides increased situational awareness for the user and/or a third party responder. For example, if the impact detection sensors detect a projectile contact at a zone near to or located at the arm, and the GPS sensors (e.g., geolocation sensors) determine that the user is still moving, the third party responder receiving this sensor data information may determine that the person is not in need of immediate attention. However, if the impact detection sensors detect a projectile contact at a zone near to or located at the heart, and the orientation and acceleration sensors determine that the user is not moving and/or is in a prone position, a third party responder receiving this sensor data information may determine that the user may be in need of immediate attention. In some instances, by combining the sensor data, the information processing unit can determine false positives and false negatives by corroborating the severity of the injury between multiple types of sensors. For example, if a heart rate sensor does not detect a heart rate of the user, but the geolocation or GPS sensor detects movement of the user and/or an upright, standing position of the user, the device can notify the user and/or a third party responder that the absence of a heart rate signal may be false or in error.

Wearable Device

Featured are peripheral devices programmed with software (e.g., an application) or capable of accessing software remotely (e.g., via a cloud- or internet-accessible server) configured to interact with a wearable device including one or more sensors. The wearable device can be worn by any subject, such as a human or another mammal (e.g., a dog). Exemplary wearable devices that may be used with the devices, systems, and methods described herein are described, e.g., in PCT Publication No. WO2015183470 and PCT Application No. PCT/US2018/033241, the disclosures of which are hereby incorporated by reference in their entirety.

The wearable device may include a networked layer of one or more (e.g., 2, 3, 4 5, 6, 7, 8, 9, 10, or more) interconnected bladders that can be individually (or in groups) inflated and deflated. An additional set of one or more (e.g., 2, 3, 4 5, 6, 7, 8, 9, 10, or more) sensors or a pressure sensitive layer senses impacts to the device or penetration of objects through the device, which may pass into the body of the wearer, triggers (e.g., automatically) the inflation of the bladders to seal off the site of penetration, and maintains pressure on the site, e.g., until attention can be given to the wearer (e.g., emergency care). The inflation of the bladders may be triggered by the impact detection sensors. When the sensors detect an impact above a predetermined threshold, the sensors relay this information to the peripheral device. The processors in the peripheral device (or at the remote location) perform a computer implemented method which identifies the impact detection stimulus and outputs a direction to trigger inflation of the bladders.

The inflation of the device may also be triggered manually. The device may feature elastic materials that maintain the structural integrity of the device, while achieving a balance between rigidity required for wound pressure and immobilization and flexibility required to accommodate rapidly filling inflatable bladders and user comfort. Furthermore, the wearable device may be designed with modular components such that all components are easily removable for replacement and/or washing the wearable device.

The wearable device may be used for controlling bleeding from severed or damaged peripheral blood vessels. The wearable device may be used to stabilize a subject (e.g., for transport or in cases where medical attention cannot be provided immediately). The methods and wearable devices described herein can be used to stabilize the patient by, e.g., controlling bleeding from a damaged vessel and/or by providing stabilization of a broken or fractured bone. Also, the methods and devices may be used to assist in increasing perfusion pressure to the heart and brain in a number of disease states, such as hemorrhagic shock, cardiogenic shock, and cardiac arrest.

The wearable device may also be configured as a wearable garment (e.g., a vest, pants, sleeve, wrap, full-body suit, sock, helmet, glove, or brace). They may also provide an automated emergency treatment for controlling or reducing fluid loss (e.g., loss of blood by hemorrhage) in places where compression is needed but where a tourniquet is not desired or cannot be used or where control by manual compression may be difficult.

The wearable device may minimize (e.g., reduce or eliminate) fluid loss from an object or individual (e.g., loss of blood by hemorrhage) caused by an impact. This includes inflating one or more (e.g., two or more, three or more, four or more, five or more, ten or more, twenty or more, fifty or more) of the bladders in the device in response to the impact, whereby inflation of the bladders at the site of the impact minimizes the fluid loss by applying pressure at the impact site. The device may reduce fluid loss by 50% or more (e.g., 60%, 70%, 80%, 90%, or 100%) at the site of impact from the time of impact, after activation and inflation of the bladders. The fluid loss may decrease by 50% or more (e.g., 60%, 70%, 80%, 90%, or 100%) after 2 seconds or more (e.g., 5 seconds, 10 seconds, 30 seconds, 60 seconds) from the time of impact, after activation and inflation of the bladders.

The wearable device can be configured to act as a tourniquet, e.g., if a limb is severely wounded or lost (e.g., due to a bomb or other blast). Alternatively, or in addition, the devices of the invention may provide an automated stabilization system that can be used to stabilize all or a portion of the body (e.g., by restricting movement (e.g., for transportation purposes or when medical attention may be delayed), such as in the case of a broken or fractured bone). Alternatively, or in addition, the devices of the invention may provide buoyancy, for example, if used in a diving suit to keep an unconscious user afloat. The invention may also be used to immobilize a head, neck, or torso of a user, following a traumatic brain injury or spinal cord injury.

The wearable device can promote survival during the "golden hour." After an object penetrates and damages the user's tissue and blood vessels the device can apply pressure to the site of the wound in order to reduce or stop the loss of blood. Preferably the user is wearing the device prior to receiving the wound. When damage to the user occurs, the system will automatically provide on-site treatment. The device may also be triggered manually (e.g., by the user or another person), and/or stabilize the entire body of the wounded person, e.g., for transportation purposes. The device may be a full body suit or it may be configured as a wearable garment, such as a vest, pants, sleeve, wrap, sock, helmet, glove, or brace.

The wearable device may include one or more functional layers, including, for example, the following: an inner layer, an outer layer, an impact detection layer, an optional layer that contains a wound sealant, and a pressure (on the body of the user) generating layer that includes the bladders. The layers do not need to be separate units, but rather can be combined within one layer or system (e.g., combining the detection capabilities with the wound sealant delivery system). Also, if chosen, one can incorporate only one or multiple layers (e.g., one could only have the detection layer, or the detection and the bladder layer, or only the wound sealant layer).

The impact detection system identifies the location on the body where the impact of an object occurred and may also determine the degree and severity of the impact. This data is sent to the information processing unit (e.g., in the peripheral device), which triggers the release of a pressurized medium (e.g., a gas, such as a non-flammable or an inert gas, in particular air, carbon dioxide, or argon), into the bladder system. Only the region where the impact has occurred will be pressurized in order to direct the flow of wound sealant to this site and/or to inflate only bladders in this region. The object that penetrated the layer(s) of the device may have also destroyed part of the system.

Substantially simultaneously with, or after, the impact, the bladders are pressurized in the area of the impact. The pressurized medium will inflate one or more bladders that were not destroyed by the impact and are activated by the device. The bladders are very small when deflated (e.g., an area of about 10 mm×10 mm to 50 mm×50 mm, and 1 mm to 10 mm in thickness), but will increase significantly upon inflation (e.g., up to 10 cm×10 cm to 20 cm×20 cm and 1 cm to 10 cm in thickness). The bladders are connected within a network, e.g., a network of tubing or similar structure. Any airtight or semi-airtight network of channels will function as a type of tubing, such as laminating or tightly weaving together two fabrics. The flow resistance in the network is equal to or higher than the forces required to inflate the bladders.

The pressure inside the balloon will depend on the type of material, and the thickness and geometry used in order to allow for such an increase in size, but will typically be around 20 psi. Depending on the design choice however, balloons similar to the ones used in angioplasty may be used as well, with nominal pressures typically ranging from 90-120 psi.

The information processing unit (e.g., in the peripheral device) may also trigger the transmission of data, such as an emergency beacon signal, that may be used to indicate the location of the user, e.g., using a global positioning module incorporated into the device. It may also process data from body sensors (e.g., to measure heart rate, etc.), if integrated.

In case of an electrical system malfunction, or if desired by the user or another person, the device can also be activated using a manual override. The manual override can be used to trigger all or a part of the system. For example, a rip cord having a handle attached thereto may be positioned on a front portion of the wearable device and connected with the valve system of the pressurized medium, such that the person wearing the device can manually open the valve to release the pressurized medium therefrom.

The device can be fabricated with modular components. All components (e.g., layers, sensors, bladders, processing units, gas cartridges, and other accessories or additional components) can be easily removed in modular fashion. For example, the information processing unit (e.g., peripheral device) may be removed such as in. If a component breaks or is damaged through use or through normal wear and tear, it can be removed or replaced. Furthermore, components can be separated from the device so the fabric of the device (e.g., the wearable garment) can be washed.

Sensors

The devices described herein (e.g., wearable devices or devices configured for use with a piece of equipment, such as a vehicle) may include one or more sensors, such as sensors for measuring impact, temperature, moisture level, pressure, acceleration, and vital sign information, such as heart rate, blood pressure, or similar indicia. These sensors may transmit information to the peripheral device that is displayed on a graphical user interface thereof. The sensor data can be processed by the information processing unit and the data can be stored non-transiently and/or transformed into a useful output indicative of the health state of a subject. The sensors may be powered by a power source or energy unit, and they may send their data to the information processing unit (e.g., in the peripheral device or at a remote location). Physiological sensors may be attached to or located on or within the wearable device, and may be operably engaged to the wearer for generating physiological signals corresponding to selected physical conditions of the user. The data from sensors may be processed by the application to trigger a distress signal. The distress signal may include information corresponding to the physiological signals. For example, the physiological sensor may be a thermometer for measuring the body temperature of the user and the distress signal may include information about the body temperature of the user. The physiological sensor may be a blood pressure meter for measuring the blood pressure of the user and the distress signal may include information about the blood pressure of the user.

The sensors may use electrocardiography to measure heart rate, a pulse oximeter to measure oxygen saturation levels, or a temperature sensor to measure body temperature. The sensors may be strategically placed near a certain organ or organ group (e.g., kidneys, heart, and brain) to track certain physiological parameters associated with a specific organ. For example, a sensor or set of sensors can be placed near the heart to track heartbeat. The location of these sensors can also be used to transmit information to the user of the device or to a third party upon activation of these sensors (e.g., when a value of the sensor output passes above or below a predetermined threshold). For example, if a set of sensors placed near the heart detects a drop in heartrate (e.g., with electrocardiography), the device would activate to send a distress signal to a third party responder. The software of the peripheral device or the information processing unit can link the sensors to their respective organs. The sensors may also detect a rupture of the wearable garment and generate a signal on the graphical user interface via the software application (e.g., as part of the programming of the application).

The device may be configured with one or more accelerometers, gyroscopes, magnetometers, barometers, relative humidity sensors, bioimpedance sensors, thermometers, biopotential sensors, or optical sensors. Accelerometers (e.g., ADLX345 chip) may be used to track steps, gait, activity, ballistocardiography, heart rate, heart rate volume, relative stroke volume, and respiration rate. A gyroscope (e.g., L3G4200D chip) may be used to track rotation and balance. A magnetometer (e.g., MC5883L chip) may be used to perform magnetoencephalography by recording magnetic currents and electrical circuits. A barometer (e.g., BMP085 chip) may be used to measure pressure. A relative humidity sensor (e.g., Si7023 chip) may be used to measure relative humidity. A bioimpedance sensor (e.g., AFE4300 chip) may be used to measure body composition and EIM. A thermometer (e.g., BMP085 chip) may be used to measure temperature. A biopotential sensor (e.g., HM301 D chip) may be used to measure electroencephalography (EEG), electromyography (EMG), echocardiography (EKG), heart rate, heart rate volume, and pulse transit time (blood pressure). An optical sensor (e.g., MAX30100 chip) may be used to measure pulse oxygenation and blood pressure. A photoplethysmography sensor or electrocardiogram (ECG) sensor may be used to track heart rate. A light sensor may be used to measure pulse oximetry (e.g., blood oxygen saturation).

If the device is configured for use with equipment, such as a machine or vehicle, sensors may also include sensors for speed, oil pressure, and altitude, among others.

Any of the sensors described above may be configured to transmit various data, e.g., to an information processing unit or a peripheral device. The peripheral device running an application can then use an algorithm to convert the physiological data into biofeedback indicia on a user or the operational data into status indicia for equipment. The biofeedback indicia may then be rendered on a graphical user interface (e.g., of the peripheral device) for visualization by the user, another user, a central command unit, a team member, or a third party responder. The sensors may track essential vital signs, such as heart rate, blood pressure, orientation, and temperature, to provide critical information for assessing the health state of a user wearing a device containing the sensors. These sensors may be integrated into the device and configured to interact with the peripheral device and/or information processing unit, e.g., by transmitting the biofeedback data (e.g., via Bluetooth) to the peripheral device, a graphical user interface, or a third party. By communicating these vital biofeedback indicia, the wearable device and/or the peripheral device can provide information, e.g., to a user or a third party responder, about the nature and severity of an impact or injury to a wearer of the device.

EXAMPLES

Example 1. Responding to an Injured Team Member

Each member of a team of four operators puts on a wearable device configured to interact with (e.g., via Bluetooth or other wireless connection) a peripheral device. The peripheral device is configured to run a smartphone application that processes sensor data obtained from sensors on the wearable device during an event (e.g., a combat mission). Each individual device can have a GPS sensor that transmits the GPS location to each user within the team. Each device can have an integrated activity sensor, an integrated respiration sensor, an integrated heart sensor, and integrated impact sensors. Each device can communicate via Bluetooth with the individual team member's smartphone running the application and can visually display all of the indicia from the various sensors, as well as GPS information (FIG. 3). The smartphone is able to communicate (e.g., via radio, e.g. TW-400) with the smartphones of the other users (users 2-4) to maintain situational awareness. Each user can also communicate to a central command portal or to a third party responder.

As shown in FIG. 10, a high impact velocity detected on the lower left side of the torso of user 1 can be displayed on a graphical user interface (FIG. 8). The impact detection sensors can identify the precise region where the impact occurred and the velocity of the ballistic impact. The wearable device can then activate the inflatable bladders and can immediately apply pressure on the wound. By processing the data from the impact detection sensors, the peripheral device is able to calculate the projectile weight and caliber of the projectile causing the impact (FIG. 11). Once the high velocity impact is detected, the system can send out the impact location on the body and the user information to the other team members and can begin to continuously transmit vital sign information, including heart rate and respiration rate.

Another team member can identify that the first team member has been injured and can locate the user on the map. He can follow the injured team member's GPS location on the graphical user interface of his own peripheral device, which can be in communication with his own wearable device. When he arrives at the injured team member, he can click on the location of the user on the map shown on his peripheral device to obtain information about the injured user (FIG. 12). He can begin to input details about the injured user on the touch screen of his user interface. He can identify that the injury was caused by an RPG (FIG. 13) and can input this information into the application running on his peripheral device. The application can begin to fill out an electronic user information card with the information input by the responder. He may identify a second injury on the right arm (FIG. 15) and can perform some routine medical tests to check the injured user's blood pressure and pain scale (FIG. 16). He can apply a pressure dressing to the arm wound (FIG. 17) and can administer an antibiotic to the injured user to prevent rapid onset of infection (FIG. 20). After stopping the bleeding in the torso and the right arm, he can put the arm in a splint (FIG. 21) and can enter an additional note that the injured team member is diabetic (FIG. 22).

The sensors of the wearable device can also be used to sense if the condition of the injured user deteriorates. If the bladders exerting pressure on the torso wound fail to prevent a drop in blood pressure, the sensors can detect this change. The blood pressure can be continuously monitored and displayed on the graphical user interface and of the peripheral device. An alert can sound when the blood pressure drops to a dangerous level. The responder can immediately recognize that a medical evacuation is necessary. The responder can input the GPS location of the injured user in the application by clicking on the map on the user interface (FIG. 23) and can transmit the electronic user information card of the injured team member to another user or a third-party responder, such as a medical evacuation team (FIG. 22). He can alert the medical evacuation team that the situation is urgent (FIG. 25), a ventilator is required for the injured team member (FIG. 26), and that an enemy troop is located nearby, requiring the evacuation team to proceed with caution (FIG. 28). He can mark the pickup zone with a panel (FIG. 29) and can send a finalized alert message. He can input his radio frequency for an additional line of communication while awaiting evacuation. The medical evacuation team may then arrive in a helicopter prepared with the necessary treatment accessories based on the user's injuries. The evacuation team can also be equipped with insulin to treat the injured member's diabetes. The medical team can resuscitate the user and can transport him to the local base hospital.

Example 2. Responding to a Vehicle Under Duress

A military vehicle is equipped with a vehicle device including a plurality of impact detection sensors located throughout the surface and interior of the vehicle. The vehicle is transporting four troops to their base when the vehicle passes over a landmine that explodes. The front right tire and the hood of the vehicle are destroyed. The engine is still working. A third party mechanic operating a peripheral device configured to run or access an application can be alerted that the vehicle has been struck. The sensor data can be processed by the application to indicate to the mechanic that the destruction of the vehicle was caused by a high force impact (e.g., landmine) and can indicate exactly where on the vehicle the impact struck. The mechanic can arrive to tend to the broken vehicle, and he may come with a spare tire. As the mechanic arrives, the broken vehicle experiences multiple bullet impacts to the windows of the car. The mechanic operating the peripheral device can immediately detect that the bullets are coming from an enemy in a tower, which is located 300 yards away and about 20 yards high. The mechanic can signal for backup and alerts the troops in the broken vehicle. The backup arrives and fends off the enemy in the tower, while the mechanic fixes the vehicle and changes the tire. When finished, the four troops in the vehicle can resume operation and transport all parties safely back to the base.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A computer implemented method for presenting physiological data regarding a health state of a subject, wherein the method is performed using an application operating on a peripheral device comprising a graphical user interface, the method comprising:
    receiving the physiological data by the peripheral device, wherein the physiological data comprise information generated upon activation of at least one impact detection sensor located within or on a wearable device that is adorned by the subject, wherein the wearable device comprises a plurality of non-overlapping zones, each of which comprises at least one said impact detection sensor, wherein said at least one impact detection sensor of each of the plurality of zones is configured to independently activate upon an impact thereto, and each said impact detection sensor is independently connected to an information processing unit (IPU) that produces the information;
    displaying on the graphical user interface a visual representation of the plurality of zones of the wearable device; and
    displaying a signal in at least one of the plurality of zones of the visual representation corresponding to activation of at least one said impact detection sensor of the wearable device, wherein the signal identifies the occurrence of a physical impact to the wearable device within at least one of the plurality of zones, thereby indicating the health state of the subject; and
    wherein the physiological data displayed on the graphical user interface further comprise one or more of ballistic impact site, impact force, and source or direction of impact.

2. The computer implemented method of claim 1, wherein:
    a) the physiological data further comprise one or more of injury type, geolocation, body position, respiratory rate, heart rate, and blood pressure; and/or
    b) the wearable device further comprises one or more sensors selected from the group consisting of a blood flow sensor, a temperature sensor, a heart rate sensor, a blood pressure sensor, an oxygen saturation sensor, and a vital sign monitoring (VSM) sensor, and wherein the method further comprises receiving by the peripheral device physiological data produced by the one or more sensors.

3. The computer implemented method of claim 1, wherein the wearable device further comprises one or more inflatable bladders and wherein the method further comprises activating inflation of the one or more inflatable bladders of the wearable device via the peripheral device in response to the physiological data.

4. The method of claim 3, wherein the peripheral device is configured for use by a person other than the subject and wherein activating inflation of the one or more bladders on the wearable device is performed by the person.

5. The computer implemented method of claim 1, wherein the application comprises a mode:
    a) that displays a map comprising a geographical location of the subject;
    b) that displays information of the subject;
    c) that displays a system status;
    d) that displays one or more system settings;
    e) that displays a cause of injury to the subject;
    f) that displays a location of injury on the subject;
    g) that displays signs and/or symptoms of the subject;
    h) that displays one or more treatments performed on the subject;
    i) that displays one or more medicines administered to the subject;
    j) that continuously displays physiological data of the subject;
    k) to transmit the physiological data of the subject to a third party responder; and/or
    l) to request medical evacuation of the subject.

6. The computer implemented method of claim 5, wherein:
    a) the map further comprises a geographical location of one or more other users;
    b) the information comprises one or more of name, age, date, time, unit, blood type, and allergy of the subject;
    c) the system status comprises one or more of power, connectivity signal, impact detection sensor status, and VSM sensor status of the wearable device or the peripheral device;
    d) the one or more system settings comprises an on/off switch and/or a sensitivity toggle for the wearable device;
    e) the injury is caused by artillery, a burn, a fall, a grenade, a gunshot wound, an improvised explosive device, a landmine, a motor vehicle collision, or a rocket propelled grenade;
    f) the location of injury comprises one or more of head, arm, leg, torso, and back;
    g) the signs and/or symptoms include one or more of time, blood pressure, pulse and oxygen saturation, alert, voice, pain, unresponsive (AVPU), and pain scale;
    h) the one or more treatments comprises one or more of extremity tourniquet, junctional tourniquet, pressure dressing, hemostatic dressing, intact, cricothyrotomy (CRIC), supraglottic airway (SGA), nasopharyngeal airway (NPA), endotracheal tube, oxygen, chest tube, chest seal, needle injection, fluid administration, blood transfusion, combat pill pack, eye shield, splint, and hypothermia prevention;

i) the one or more medicines comprises an analgesic or antibiotic;
j) the physiological data is heart rate and/or respiration rate; and/or
k) the mode to request medical evacuation transmits information of the subject comprising one or more of geolocation, radio frequency, nationality, treatment status, military status, special equipment request, wartime security status, method of site marking, and site contamination status.

7. The computer implemented method of claim 6, wherein:
a) the treatment status comprises urgent, urgent surgery required, priority, routine, or convenience;
b) the nationality comprises US or non-US;
c) the military status comprises military, civilian, or enemy prisoner of war;
d) the special equipment request comprises a hoist, extraction equipment, or a ventilator;
e) the wartime security status comprises no enemy troops, possible enemy, enemy in area and proceed with caution, or enemy in area and armed escort required;
f) the method of site marking comprises a panel, pyrotechnic signal, or a smoke signal; and/or
g) the site contamination status comprises chemical, biological, radiological, or nuclear contamination.

8. The computer implemented method of claim 1, wherein:
a) the application comprises a security feature;
b) the physiological data are stored on a cloud-based device or a server; and/or
c) the graphical user interface is a touch screen graphical user interface.

9. The computer implemented method of claim 1, wherein the peripheral device comprises one or more processors coupled to the display.

10. The computer implemented method of claim 9, wherein the peripheral device comprises a non-transient memory storing instructions that, when executed by the one or more processors, causes the one or more processors to perform one or more operations related to the physiological data.

11. The method of claim 1, wherein the physiological data are displayed to the subject or a different person.

12. The method of claim 11, wherein the different person is a team member or a third party responder.

13. A peripheral device comprising:
a display;
one or more processors coupled to the display; and
a non-transient memory storing instructions that, when executed by the one or more processors, causes the one or more processors to perform operations comprising:
rendering a graphical user interface in the display;
processing information received from a wearable device to produce physiological data, the wearable device comprising at least one impact detection sensor located within or on a wearable device that is adorned by the subject, wherein the wearable device comprises a plurality of non-overlapping zones, wherein each of said plurality of zones comprises at least one said impact detection sensor, wherein each said impact detection sensor is configured to independently activate upon an impact thereto, and wherein each said impact detection sensor is independently connected to an information processing unit (IPU) that produces the information upon activation of at least one said impact detection sensor; and
displaying the physiological data on the graphical user interface, wherein the displaying comprises producing a visual representation of the plurality of zones of the wearable device and, following activation of at least one said impact detection sensor of the wearable device, displaying a signal in each of the plurality of zones of the visual representation that correspond to activation of each said impact detection sensor of the wearable device, wherein the signal identifies the occurrence of a physical impact to the wearable device within at least one of the plurality of zones, thereby indicating the health state of the subject;
wherein the physiological data displayed on the graphical user interface further comprise one or more of ballistic impact site, impact force, source or direction of impact.

14. The peripheral device of claim 13, wherein the physiological data further comprise one or more of injury type, geolocation, body position, respiratory rate, heart rate, and blood pressure.

15. The peripheral device of claim 13, wherein the peripheral device is configured to display the physiological data to a subject wearing the wearable device or a different person.

16. The peripheral device of claim 15, wherein the different person is a team member or a third party responder.

17. The peripheral device of claim 13, wherein the peripheral device is configured to perform the computer implemented method of claim 1.

18. A system comprising the peripheral device of claim 13 and the wearable device.

19. A system comprising a plurality of the peripheral devices of claim 13, each of which is independently running the application.

20. The system of claim 19, wherein the plurality of peripheral devices is configured to communicate with each other.

21. The system of claim 19, further comprising a plurality of the wearable devices, each of which is independently configured to communicate with any one, or all, of the plurality of peripheral devices.

22. The system of claim 21, wherein:
a) each of the plurality of peripheral devices is configured to control or communicate with any one, or all, of said plurality of the wearable devices; or
b) a designated one of the plurality of peripheral devices is configured to control or communicate with a designated one of said plurality of the wearable devices.

23. The system of claim 21, wherein the communication comprises transmission of physiological data or other indicia regarding one or more users of the system.

24. The peripheral device of claim 13, wherein the wearable device comprises one or more inflatable bladders and the peripheral device comprises an input for activating inflation of the one or more inflatable bladders in the wearable device.

25. The peripheral device of claim 13, wherein the peripheral device is configured for wired or wireless communication with the wearable device.

* * * * *